(12) United States Patent
Haverkost et al.

(10) Patent No.: US 11,129,702 B2
(45) Date of Patent: Sep. 28, 2021

(54) PEDAL ACCESS EMBOLIC FILTERING SHEATH

(71) Applicant: BOSTON SCIENTIFIC SCIMED, INC., Maple Grove, MN (US)

(72) Inventors: Patrick A. Haverkost, Corcoran, MN (US); Amelia Ann Sandberg, Fridley, MN (US); Joel N. Groff, Delano, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 321 days.

(21) Appl. No.: 16/407,468

(22) Filed: May 9, 2019

(65) Prior Publication Data

US 2019/0343613 A1  Nov. 14, 2019

Related U.S. Application Data

(60) Provisional application No. 62/668,870, filed on May 9, 2018.

(51) Int. Cl.
| | | |
|---|---|---|
| *A61F 2/01* | (2006.01) | |
| *A61B 17/3207* | (2006.01) | |
| *A61M 25/10* | (2013.01) | |

(52) U.S. Cl.
CPC .......... *A61F 2/014* (2020.05); *A61B 17/3207* (2013.01); *A61F 2/011* (2020.05); *A61F 2002/018* (2013.01); *A61M 25/10* (2013.01)

(58) Field of Classification Search
CPC .......... A61F 2/014; A61F 2/011; A61F 2/013; A61F 2002/018; A61B 17/3207; A61B 17/320758; A61B 17/320725; A61M 25/10; A61M 25/1009; A61M 2025/1081
See application file for complete search history.

(56) References Cited

U.S. PATENT DOCUMENTS

| | | |
|---|---|---|
| 3,472,230 A | 10/1969 | Fogarty |
| 3,592,186 A | 7/1971 | Oster |
| 3,683,904 A | 8/1972 | Forster |

(Continued)

FOREIGN PATENT DOCUMENTS

| | | |
|---|---|---|
| DE | 2821048 C2 | 7/1980 |
| DE | 4030998 A1 | 4/1991 |

(Continued)

OTHER PUBLICATIONS

"Endovascular Grafts, Stents Drive Interventional Radiology Growth," Cardiovascular Device Update, 2(3):1-12(Mar. 1996).

(Continued)

*Primary Examiner* — Erich G Herbermann
*Assistant Examiner* — Chima U Igboko
(74) *Attorney, Agent, or Firm* — Seager, Tufte & Wickhem LLP

(57) ABSTRACT

A filtering sheath includes an elongated tubular member defined by a circumferential wall and having a distal end, a proximal end, and a lumen extending therebetween. The distal end has a plurality of slits extending through the circumferential wall, the plurality of slits defining an expandable filter region. The plurality of slits are arranged in a pattern that allows the expandable filter region to move between a first, contracted configuration, and a second, expanded configuration.

2 Claims, 22 Drawing Sheets

(56) References Cited

U.S. PATENT DOCUMENTS

| | | |
|---|---|---|
| 3,889,657 A | 6/1975 | Baumgarten |
| 3,952,474 A | 4/1976 | Rice |
| 3,996,938 A | 12/1976 | Clark, III |
| 4,046,150 A | 9/1977 | Schwartz et al. |
| 4,425,908 A | 1/1984 | Simon |
| 4,447,227 A | 5/1984 | Kotsanis |
| 4,580,568 A | 4/1986 | Gianturco |
| 4,590,938 A | 5/1986 | Segura et al. |
| 4,619,246 A | 10/1986 | Molgaard-Niielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,665,918 A | 5/1987 | Garza et al. |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,832,028 A | 5/1989 | Patel |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,898,575 A | 2/1990 | Fishcell et al. |
| 4,907,336 A | 3/1990 | Gianturco et al. |
| 4,921,478 A | 5/1990 | Solano et al. |
| 4,921,483 A | 5/1990 | Wijay et al. |
| 4,921,484 A | 5/1990 | Hillstead |
| 4,926,858 A | 5/1990 | Gifford, III et al. |
| 4,950,277 A | 8/1990 | Farr |
| 4,955,895 A | 9/1990 | Sugiyama al. |
| 4,957,482 A | 9/1990 | Shiber |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold et al. |
| RE33,569 E | 4/1991 | Gifford et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,044 A | 10/1991 | Mueller et al. |
| 5,054,500 A | 10/1991 | Littleford et al. |
| 5,071,407 A | 12/1991 | Termin et al. |
| 5,071,425 A | 12/1991 | Gifford et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell et al. |
| 5,102,415 A | 4/1992 | Guenter et al. |
| 5,104,399 A | 4/1992 | Lazarus |
| 5,108,419 A | 4/1992 | Reger et al. |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,329,942 A | 7/1994 | Gunther et al. |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebrve |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazarus |
| 5,405,377 A | 4/1995 | Cragg |
| 5,409,454 A | 4/1995 | Fischell et al. |
| 5,415,630 A | 5/1995 | Gory et al. |
| 5,419,774 A | 5/1995 | Willard et al. |
| 5,421,832 A | 6/1995 | Lefebrve |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 5,456,667 A | 10/1995 | Ham et al. |
| 5,462,529 A | 10/1995 | Simpson |
| 5,476,104 A | 12/1995 | Sheahon |
| 5,484,418 A | 1/1996 | Quiachon et al. |
| 5,507,767 A | 4/1996 | Maeda et al. |
| 5,512,044 A | 4/1996 | Duer |
| 5,527,354 A | 6/1996 | Fontaine et al. |
| 5,536,242 A | 7/1996 | Willard et al. |
| 5,540,707 A | 7/1996 | Ressemann et al. |
| 5,549,626 A | 8/1996 | Miller et al. |
| 5,562,724 A | 10/1996 | Vorwerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,669,933 A | 9/1997 | Simon et al. |
| 5,695,519 A | 12/1997 | Summers et al. |
| 5,709,704 A | 1/1998 | Mott et al. |
| 5,720,764 A | 2/1998 | Naderlinger |
| 5,728,066 A | 3/1998 | Daneshvar |
| 5,746,758 A | 5/1998 | Nordgren et al. |
| 5,779,716 A | 7/1998 | Cano et al. |
| 5,792,300 A | 8/1998 | Inderbitzen et al. |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,810,874 A | 9/1998 | Lefebrve |
| 5,814,064 A | 9/1998 | Daniel et al. |
| 5,817,102 A | 10/1998 | Johnson et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,876,374 A * | 3/1999 | Alba ............... A61F 2/958 604/164.08 |
| 5,893,867 A | 4/1999 | Bagaoisan et al. |
| 5,895,399 A | 4/1999 | Barbut et al. |
| 5,902,263 A | 5/1999 | Patterson et al. |
| 5,906,618 A | 5/1999 | Larson, III |
| 5,908,435 A | 6/1999 | Samuels |
| 5,910,154 A | 6/1999 | Tsugita et al. |
| 5,911,734 A | 6/1999 | Tsugita et al. |
| 5,916,193 A | 6/1999 | Stevens et al. |
| 5,925,016 A | 7/1999 | Chornenky et al. |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |
| 5,938,645 A | 8/1999 | Gordon |
| 5,938,672 A | 8/1999 | Nash |
| 5,941,869 A | 8/1999 | Patterson et al. |

(56) References Cited

U.S. PATENT DOCUMENTS

| | | |
|---|---|---|
| 5,941,896 A | 8/1999 | Kerr |
| 5,947,995 A | 9/1999 | Samuels |
| 5,951,585 A | 9/1999 | Cathcart et al. |
| 5,954,745 A | 9/1999 | Gertler et al. |
| 5,976,172 A | 11/1999 | Homsma et al. |
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,022,336 A | 2/2000 | Zadno-Azizi et al. |
| 6,027,520 A | 2/2000 | Tsugita et al. |
| 6,051,014 A | 4/2000 | Jang |
| 6,053,932 A | 4/2000 | Daniel et al. |
| 6,059,814 A | 5/2000 | Ladd |
| 6,066,158 A | 5/2000 | Engelson et al. |
| 6,068,645 A | 5/2000 | Tu |
| 6,077,295 A | 6/2000 | Limon et al. |
| 6,080,170 A | 6/2000 | Nash et al. |
| 6,086,605 A | 7/2000 | Barbut et al. |
| 6,129,739 A | 10/2000 | Khosravi |
| 6,131,991 A | 10/2000 | Muni et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,231,588 B1 | 5/2001 | Zadno-Azizi |
| 6,258,115 B1 | 7/2001 | Dubrul |
| 6,270,477 B1 | 8/2001 | Bagaoisan et al. |
| 6,295,990 B1 | 10/2001 | Lewis et al. |
| 6,398,773 B1 | 6/2002 | Bagaoisan et al. |
| 6,443,926 B1 | 9/2002 | Kletschka |
| 6,485,500 B1 | 11/2002 | Kokish et al. |
| 6,540,722 B1 | 4/2003 | Boyle et al. |
| 6,544,276 B1 | 4/2003 | Azizi |
| 6,569,148 B2 | 5/2003 | Bagosian et al. |
| 6,605,074 B2 | 8/2003 | Zadno-Azizi et al. |
| 2001/0049517 A1 | 12/2001 | Zadno-Azizi et al. |
| 2002/0029031 A1 | 3/2002 | Bagaoisan et al. |
| 2002/0161389 A1 | 10/2002 | Boyle et al. |
| 2007/0021648 A1* | 1/2007 | Lenker .............. A61M 25/0097 600/29 |
| 2013/0144328 A1* | 6/2013 | Weber .................... A61F 2/014 606/200 |

FOREIGN PATENT DOCUMENTS

| | | |
|---|---|---|
| EP | 0200688 A1 | 11/1986 |
| EP | 0293605 A1 | 12/1988 |
| EP | 0411118 A1 | 2/1991 |
| EP | 0427429 A2 | 5/1991 |
| EP | 0437121 B1 | 7/1991 |
| EP | 0472334 A1 | 2/1992 |
| EP | 0472368 A2 | 2/1992 |
| EP | 0655228 A1 | 5/1995 |
| EP | 0686379 A2 | 6/1995 |
| EP | 0696447 A2 | 2/1996 |
| EP | 0737450 A1 | 10/1996 |
| EP | 0743046 A1 | 11/1996 |
| EP | 0759287 A1 | 2/1997 |
| EP | 0771549 A2 | 5/1997 |
| EP | 0784998 A2 | 7/1997 |
| EP | 0852132 A1 | 7/1998 |
| EP | 0934729 A1 | 11/1999 |
| FR | 2580504 A1 | 10/1986 |
| FR | 2643250 A1 | 8/1990 |
| FR | 2666980 A1 | 3/1992 |
| FR | 2768326 A1 | 3/1999 |
| GB | 2020557 A | 11/1979 |
| GB | 2020557 B | 1/1983 |
| JP | 08187294 A | 7/1996 |
| SU | 764684 A1 | 9/1980 |
| WO | 9203097 A1 | 3/1992 |
| WO | 9414389 A1 | 7/1994 |
| WO | 9424946 A1 | 11/1994 |
| WO | 9601591 A1 | 1/1996 |
| WO | 9610375 A1 | 4/1996 |
| WO | 9619941 A1 | 7/1996 |
| WO | 9623441 A1 | 8/1996 |
| WO | 9633677 A1 | 10/1996 |
| WO | 9717100 A1 | 5/1997 |
| WO | 9727808 A1 | 8/1997 |
| WO | 9802084 A2 | 1/1998 |
| WO | 9802112 A1 | 1/1998 |
| WO | 9823222 A1 | 6/1998 |
| WO | 9833443 A1 | 8/1998 |
| WO | 9836786 A1 | 8/1998 |
| WO | 9838920 A1 | 9/1998 |
| WO | 9838929 A1 | 9/1998 |
| WO | 9839046 A1 | 9/1998 |
| WO | 9846297 A1 | 10/1998 |
| WO | 9847447 A1 | 10/1998 |
| WO | 9849952 A1 | 11/1998 |
| WO | 9850103 A1 | 11/1998 |
| WO | 9851237 A1 | 11/1998 |
| WO | 9855175 A1 | 12/1998 |
| WO | 9909895 A1 | 3/1999 |
| WO | 9922673 A1 | 5/1999 |
| WO | 9923976 A1 | 5/1999 |
| WO | 9925252 A1 | 5/1999 |
| WO | 9940964 A1 | 8/1999 |
| WO | 9942059 A1 | 8/1999 |
| WO | 9944510 A1 | 9/1999 |
| WO | 9944542 A2 | 9/1999 |
| WO | 9955236 A1 | 11/1999 |
| WO | 9958068 A2 | 11/1999 |
| WO | 0007655 A1 | 2/2000 |
| WO | 0009054 A1 | 2/2000 |
| WO | 0016705 A1 | 3/2000 |
| WO | 0049970 A1 | 8/2000 |
| WO | 0145590 A2 | 6/2001 |
| WO | 0167989 A2 | 9/2001 |

OTHER PUBLICATIONS

Tunick et al., "Protruding Atheromas in the Thoracic Aortic and Systemic Embolization," pp. 423-427 American College of Physicians (1991).
Karalis et al., "Recognition and Embolic Potential Intraaortic Atherosclerotic Debris," American College of Cardiology (Jan. 1991).
Cragg, "A New Percutaneous Vena Cava Filger," AJR, 141:601-604 (Sep. 1983).
Cragg, "Nonsurgical Placement of Arterial Endoprosthesis: A New Technique Using Nitinol Wire," AJR, pp. 261-263 (Apr. 1983).
Dietrich et al., "Percutaneous Techniques for Endoluminal Cartoid Interventions," J. Endovasc. Surg; 3:182-202 (1996).
Fadali, "A Filtering Device for the Prevention of Particulate Embolization during the Course of Cardiac Surgery." Surgery, 64(3):634-639 (Sep. 1968).
Haissaguerre et al., "Spontaneous Initiation of Atrial Fibrillation by Ectopic Beats Originating in the Pulmonary Veins," The New England Journal of Medicine, 339(10):659-666 (Sep. 1988).
Lesh, "Can Catheter Ablation Cure Atrial Fibrillation?" ACC Current Journal Review, pp. 38-40 (Sep./Oct. 1997).
Lund et al., "Long-Term Patency of Ductus Arteriosus After Balloon Dialation: an Experimental Study," Laboratory Investigation, 69 (4): 772-774 (Apr. 1984).
Mazur et al., "Directional Atherectomy with the Omnicath: A Unique New Catheter System," Catheterization and Cardiovacular Diagnosis, 31: 17-84 (1994).

(56) References Cited

OTHER PUBLICATIONS

Moussa, "Stents Don't Require Systemic Anticoagulation . . . But the Technique (and Results) Must be Optimal," Journal of Invasive Cardiol; 8(E):3E-7E, (1996).
Theron et al; "New Triple Coaxial Catheter System for Cartoid Angioplasty with cerebral Protection," American Journal of Neuroradiology, 11:869-874 (1990).
Tunick et al; "Protruding Atherosclerotic Plaque in the Aortic Archo for Patients with Systemic Embolization: A New Finding Seen by Transesophageal Echocardiography," American Heart Journal 120(3):658-660 (Sep. 1990).
Wholey, Mark H. et al; PTA and Stents in the Treatment of Extracranial Circulation, The Journal of Invasive Cardiology, 8(E):25E-30E (1996).
"Atherosclerotic Disease of the Aortic Arch as a Risk Factor of Recurrent Ischemic Stroke", The New England Journal of Medicine, pp. 1216-1221, May 1996.
International Search Report and Written Opinion dated Aug. 9, 2019 for International Application No. PCT/US2019/031501.

* cited by examiner

PEDAL ACCESS EMBOLIC FILTERING SHEATH

CROSS-REFERENCE TO RELATED APPLICATIONS

This application claims the benefit of priority under 35 U.S.C. § 119 to U.S. Provisional Application Ser. No. 62/668,870, filed May 9, 2018, the entirety of which is incorporated herein by reference.

TECHNICAL FIELD

The disclosure pertains to medical devices and more particularly to embolic filtering devices for atherectomy techniques, and methods for using such medical devices.

BACKGROUND

A wide variety of medical devices have been developed for medical use including, for example, medical devices utilized to prevent blockage of small vessels by plaque particles during atherectomy techniques. These medical devices may be used in a variety of vessels including those located below the knee, and are manufactured and used according to any one of a variety of different methods. Of the known medical devices and methods, each has certain advantages and disadvantages. There is an ongoing need to provide alternative medical devices as well as alternative methods for manufacturing and using the medical devices.

SUMMARY

This disclosure provides design, material, manufacturing method, and use alternatives for medical devices. An example medical device includes a filtering sheath comprising an elongated tubular member defined by a circumferential wall and having a distal end, a proximal end, and a lumen extending therebetween, the elongated tubular member having a proximal solid walled region devoid of any openings extending through the circumferential wall, the distal end having a plurality of slits extending through the circumferential wall, the plurality of slits defining an expandable filter region, wherein the plurality of slits are arranged in a pattern that allows the expandable filter region to move between a first, contracted configuration, and a second, expanded configuration.

Alternatively or additionally to the embodiment above, the elongated tubular member, including the proximal solid walled region and the expandable filter region, is formed of a single monolithic piece.

Alternatively or additionally to any of the embodiments above, the elongated tubular member is formed from a polymer.

Alternatively or additionally to any of the embodiments above, the elongated tubular member, including the proximal solid walled region and the expandable filter region has a total length of at least 100 mm, wherein the expandable filter region has a length of less than 20 mm.

Alternatively or additionally to any of the embodiments above, the proximal end of the elongated tubular member is connected to a container configured to receive blood and debris captured by the expandable filter region.

Alternatively or additionally to any of the embodiments above, the pattern includes a plurality of sets of slits, each set including a plurality of circumferentially spaced apart longitudinal slits.

Alternatively or additionally to any of the embodiments above, each slit includes at least one non-zero angle.

Alternatively or additionally to any of the embodiments above, each slit includes two or more non-zero angles.

Alternatively or additionally to any of the embodiments above, the plurality of slits defining each set of slits has the same shape.

Alternatively or additionally to any of the embodiments above, the plurality of slits defining a first set are offset circumferentially from the plurality of slits defining a second set adjacent the first set.

Alternatively or additionally to any of the embodiments above, the pattern includes 4-15 sets of slits.

Alternatively or additionally to any of the embodiments above, the pattern includes 7-12 sets of slits.

Alternatively or additionally to any of the embodiments above, when in the expanded configuration, the plurality of slits defines a plurality of holes having a width of 5-130 microns.

Alternatively or additionally to any of the embodiments above, the plurality of holes each has a width of 70-90 microns.

An example embolic filtering assembly includes a filtering sheath comprising an elongated tubular member defined by a circumferential wall and having a distal end and a proximal end, the filtering sheath having a lumen extending longitudinally between the distal and proximal ends, the distal end having a plurality of slits extending through the circumferential wall, the plurality of slits defining an expandable filter region, wherein the plurality of slits are arranged in a pattern that allows the expandable filter region to move between a first, contracted configuration, and a second, expanded configuration, a dilation shaft having a dilator on a distal end thereof, and a balloon attached to the dilator, the dilation shaft removably disposed within the lumen of the filtering sheath, wherein the balloon is configured to inflate and expand the expandable filter region, and a locking hub attached to the proximal end of the filtering sheath and the dilation shaft.

Alternatively or additionally to any of the embodiments above, the locking hub includes a distal portion and a proximal portion, wherein the proximal portion is configured to rotate within and slide into and out of the distal portion.

Alternatively or additionally to any of the embodiments above, the distal portion of the locking hub is fixed to the filtering sheath and the proximal portion of the locking hub is fixed to the dilation shaft.

Alternatively or additionally to any of the embodiments above, the distal portion of the locking hub includes a slot and the proximal portion of the locking hub includes a tab configured to enter the slot, thereby advancing the dilation shaft and positioning the balloon within the expandable filter region of the filtering sheath.

Alternatively or additionally to any of the embodiments above, the elongated tubular member, including the expandable filter region, is formed of a single monolithic piece.

An example method of treating a lesion in a vessel using an embolic filter sheath includes inserting an embolic filter assembly into a vessel downstream from a lesion, the embolic filter assembly including a filtering sheath comprising an elongated tubular member defined by a circumferential wall and having a distal end, a proximal end, and a lumen extending therebetween, the distal end having a plurality of slits extending through the circumferential wall, the plurality of slits defining an expandable filter region, wherein the plurality of slits are arranged in a pattern that allows the expandable filter region to move between a first, contracted delivery configuration, and a second, expanded configuration, a dilation shaft having a dilator on a distal end thereof, and a balloon attached to a proximal end of the dilator, the dilation shaft removably disposed within the lumen of the filtering sheath, wherein the balloon is configured to inflate and expand the expandable filter region to the second, expanded configuration, a locking hub including a distal hub portion fixed to a proximal end of the filtering sheath, and a proximal hub portion fixed to a proximal end of the dilation shaft, wherein the proximal hub portion is movable relative to the distal hub portion. The method further includes advancing the proximal hub portion towards the distal hub portion, thereby moving the dilation shaft distally and positioning the balloon within the expandable filter region of the filtering sheath, inflating the balloon, thereby expanding the expandable filter region into contact with vessel walls, deflating the balloon and withdrawing the dilation shaft from the filtering sheath, and ablating the lesion and collecting lesion particles in the filtering sheath.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
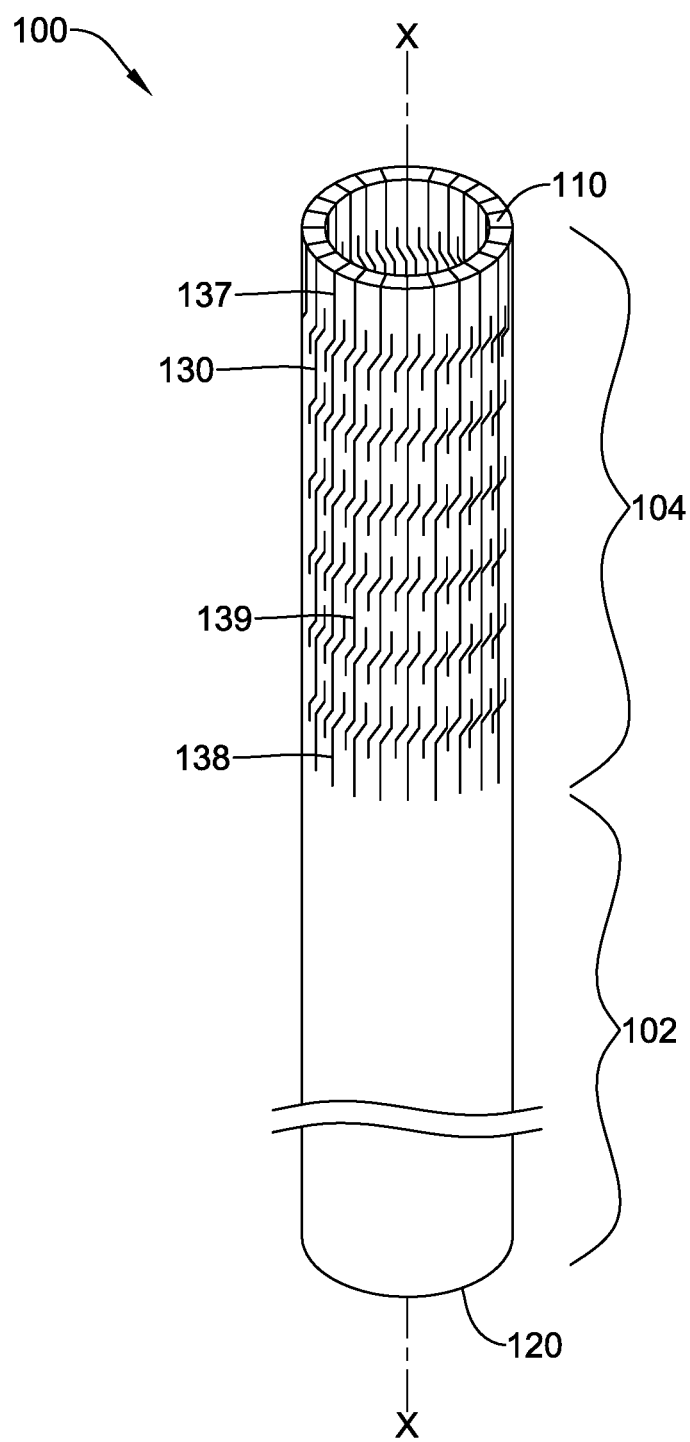
FIG. 1 illustrates an example filter sheath for use during an atherectomy procedure.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/ manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

Patients with lower limb critical limb ischemia (CLI) are traditionally treated with anterograde or contralateral retrograde femoral approaches. However, this approach may have disadvantages and difficulties. A pedal access approach may also be used. A method and device for preventing blockage of the small pedal vessels by plaque particles dislodged during atherectomy treatment is needed.

As will be described in greater detail below, FIG. 1 illustrates an example filter sheath 100 which may be utilized in an atherectomy procedure. Specifically, FIG. 1 illustrates the filter sheath 100 having a distal end 110, a proximal end 120 and which may include a solid walled region 102 and an expandable filter region 104. The solid walled region 102 extends from the proximal end 120 to the expandable filter region 104. The solid walled region 102 may be defined by a solid tubular shaft having a circumferential wall devoid of any slits, holes or openings extending through the wall.

The expandable filter region 104 may be located adjacent the distal end 110 of the filter sheath 100 and may be defined by a plurality of slits 130 extending completely through the wall of the filter sheath 100. The plurality of slits 130 allows the expandable filter region 104 to expand radially. The plurality of slits 130 may be present in a pattern and may include one or more sets of circumferentially spaced apart slits. In the example illustrated in FIG. 1, the pattern includes a set of circumferentially spaced apart distal slits 137, a set of circumferentially spaced apart proximal slits 138 and at least one set of circumferentially spaced apart middle slits 139. Each of the distal slits, 137, proximal slits 138, and middle slits 139 may be oriented generally longitudinally, as shown in FIG. 1. The generally longitudinal slits may include curves or angles, but the overall appearance of the slits is longitudinal. In other examples, the slits may have an overall appearance that is oriented generally perpendicular to, or at a non-zero angle to the longitudinal axis X-X.

Figure 2:
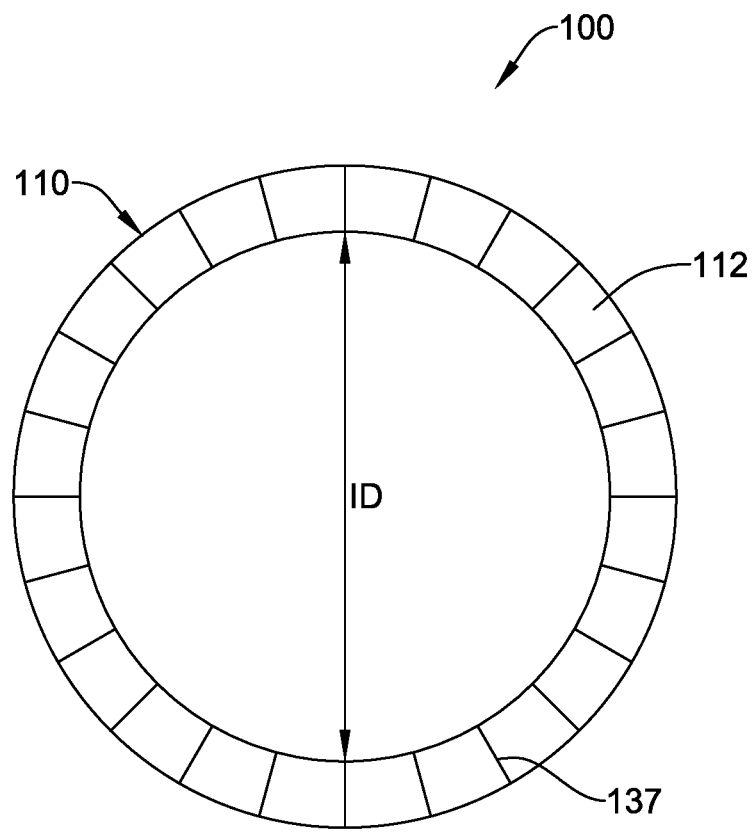
FIG. 2 is a top view of the filter sheath of FIG. 1.

FIG. 2 illustrates a top view of the distal end 110 of the filter sheath 100 having an inner diameter ID. As shown, the distal slits 137 extend to the very distal end 110 of the sheath, separating the distal end 110 into a number of separate distal sections 112. In the example shown in FIG. 2, the filter sheath 100 has twenty-four distal slits 137 that divide the distal end 110 into twenty-four distal sections 112. In the contracted state, shown in FIGS. 1 and 2, the distal sections 112 remain in contact with one another, defining a tubular structure with an inner diameter (ID).

Figure 3A:
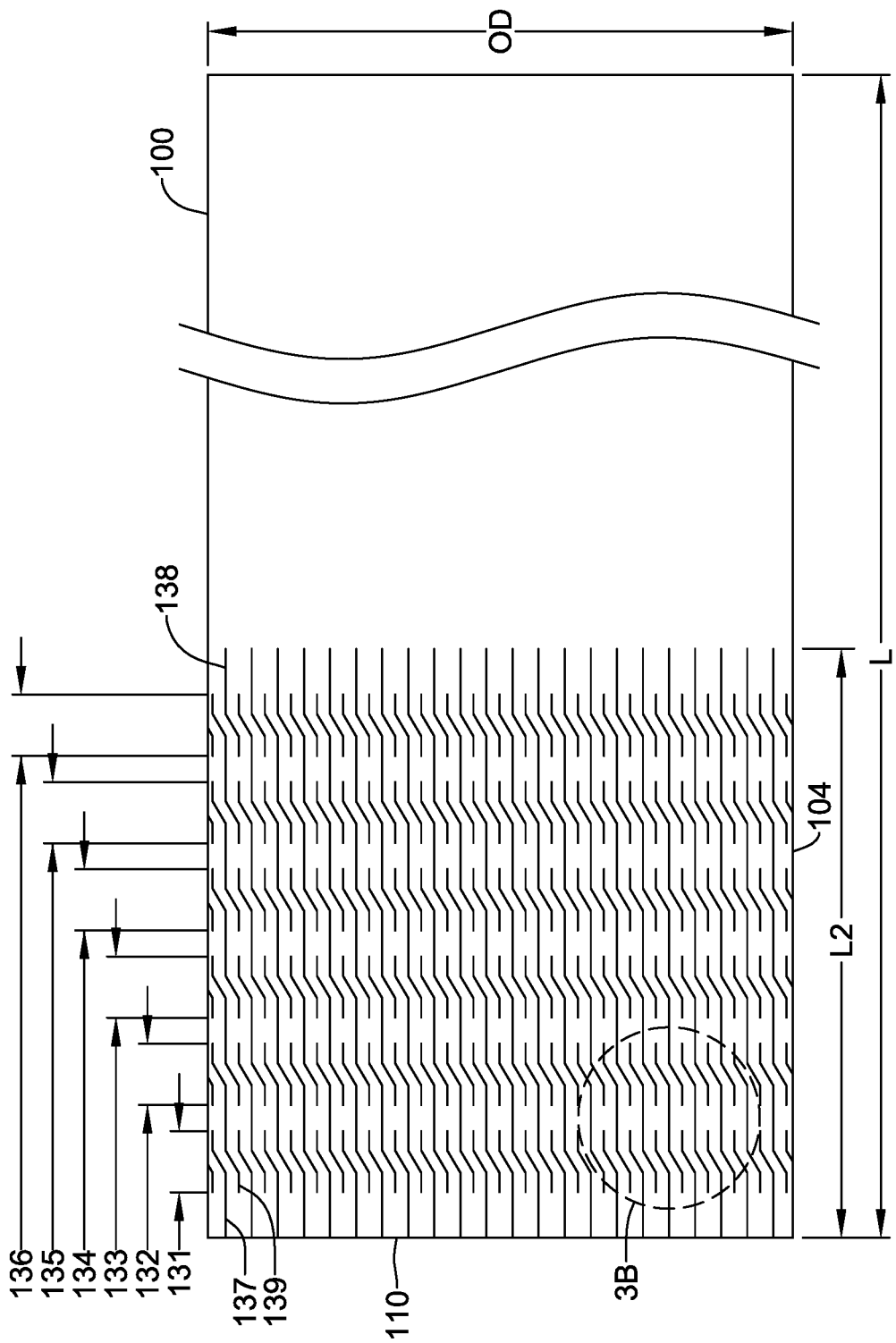
FIG. 3A illustrates a flat pattern of slits of the filter sheath of FIG. 1.

The plurality of slits 130 may form a plurality of overlap regions 131-136, as shown in FIG. 3A. As illustrated, a portion of each of the distal slits 137 overlaps a portion of a first set of middle slits 139 in overlap region 131. Similarly, a portion of the first set of middle slits 139 overlaps a portion of the next set of middle slits in overlap region 132, and so on. In some examples, the sets of middle slits 139 may be offset from one another. For example, the plurality of slits defining a first set of middle slits may be offset circumferentially from the plurality of slits defining a second set adjacent the first set.

In the example slit pattern illustrated in FIG. 3A, the distal slits 137, five sets of middle slits 139, and proximal slits 138 overlap in six overlap regions 131, 132, 133, 134, 135, and 136. In other examples, the pattern may include 4-15 sets of slits, 7-12 sets of slits, or any other number of sets of slits. Each of the six overlap regions 131-136 may have a different longitudinal length, the same longitudinal length, or some overlap regions may have the same longitudinal length and other overlap regions may have different longitudinal lengths. In one example, the first overlap region 131 may have a longitudinal length of 0.567 mm, the second overlap region 132 may have a longitudinal length of 0.546 mm, the third overlap region 133 may have a longitudinal length of 0.526 mm, the fourth overlap region 134 may have a longitudinal length of 0.507 mm, the fifth overlap region 135 may have a longitudinal length of 0.487 mm, and the sixth overlap region 136 may have a longitudinal length of 0.467 mm.

The filter sheath 100 may have a total length L of at least 100 mm. In some examples, the total length L of the filter sheath 100 may be 100 mm to 200 mm. In other examples, the total length L may be 110 mm to 150 mm. The expandable filter region 104 may have a length L2 of less than 20 mm. In some examples, the expandable filter region 104 may have a length L2 of 2 mm to 20 mm. In other examples, the expandable filter region 104 may have a length L2 of 5 mm to 10 mm. In one example, the filter sheath 100 may have a total length L of 130 mm, an outer diameter OD of 1.78 mm, an inner diameter ID of 1.41 mm, and the expandable filter region 104 may have a length L2 of 8 mm. In other examples, the filter sheath 100 may be a 4 French (1.35 mm OD) or 7 French (2.30 mm OD) insertion sheath. In additional examples, the filter sheath 100 may have an OD of 1.5 mm, expanding to 3.5 mm at the distal end 110.

Figure 5:
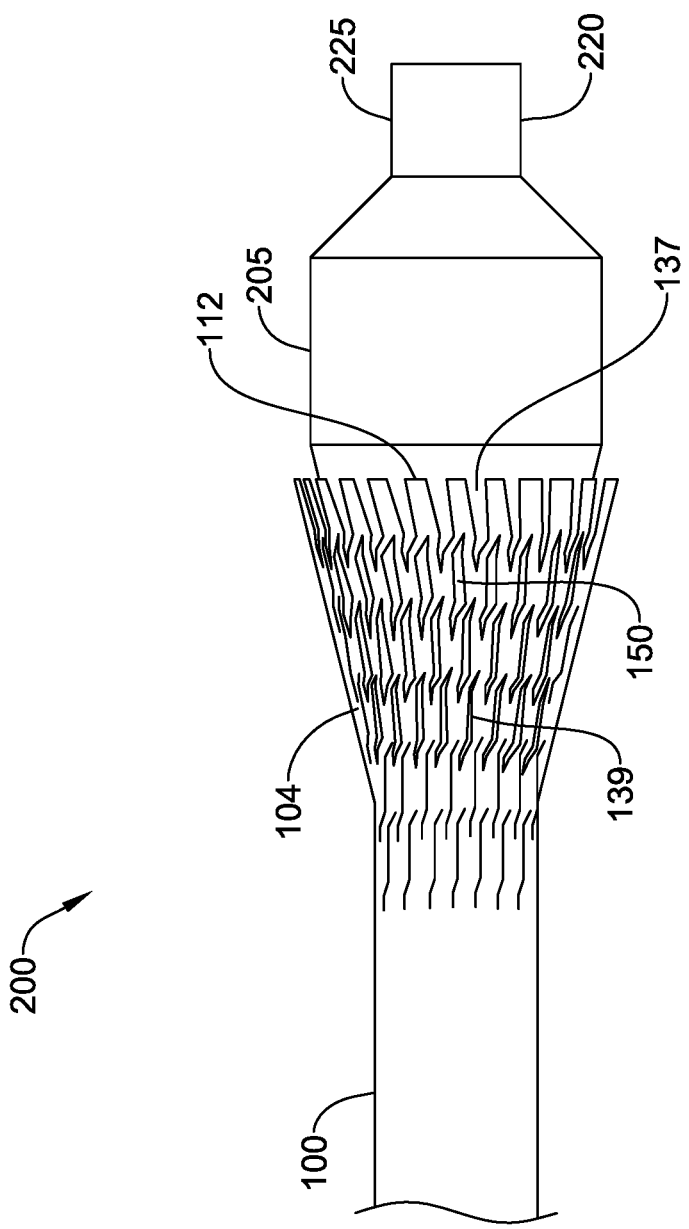
FIG. 5 illustrates the filter sheath of FIG. 4 in an expanded configuration on the expansion balloon.

In some examples, the filter sheath 100 may be made of polymer, elastomeric polyamides, block polyamide/ethers, polyether block amide (PEBA, for example available under the trade name PEBAX®), ethylene tetrafluoroethylene (ETFE), or other polymers generally used in medical catheters. In other examples, the expandable filter region 104 may be made of a shape memory material, such as nitinol or a shape memory polymer. The shape memory expandable filter region 104 may be attached to a solid walled region 102 made of a different material, or the entire filter sheath 100 may be made of a shape memory material. The entire filter sheath 100, including the expandable filter region 104 and the solid walled region 102, may be formed from a single monolithic piece. In other examples, the expandable filter region 104 may be formed from a material different from the solid walled region 102, with the two regions attached during manufacture. The slits 130 may be formed by laser cutting the distal portion of the monolithic filter sheath 100 in a pattern that, upon expansion, results in a flared distal sheath tip with small holes through which plaque particles cannot pass. The slits may be sized and spaced such that, when the expandable filter region 104 is expanded by a balloon 205, as shown in FIG. 5, openings or holes 150 will be formed and the material of the filter sheath 100 will plastically deform enough so that it will hold its expanded shape upon deflation of the balloon. The size of the holes 150 may be controlled, such that only particles under a particular size will be permitted to pass through the filter. In some examples, the holes 150 may be as small as 5 microns across. In other examples, the holes 150 may be as large as 110 to 130 microns across. In further examples, the holes 150 may be 70-90 microns across. The holes 150 may be circular or oval in cross-section, however, oval holes 150 may provide the advantage of trapping large particles in the center and trapping smaller particles at the ends of the oval. The above measurements for holes 150 apply equally to oval holes, with the measurements taken across the largest diameter.

The pattern of slits 130 may be designed such that the balloon expansion causes enough strain to stretch the material of the filter sheath 100 beyond its plastic deformation point. In some examples, the strain rate is 2-20%. In one example, the strain rate is 3%. The pattern of slits 130 may be altered and the orientation of slits may be changed from primarily longitudinal, as shown in FIG. 3, to circumferential or angled between circumferential and longitudinal.

The outer diameter of the flared, expanded distal end 110 may be sized to seal tightly against the inner wall of the vessel being treated. In some examples, the outer diameter of the expanded distal end 110 may be slightly larger than the inner diameter of the vessel being treated.

Figure 3B:
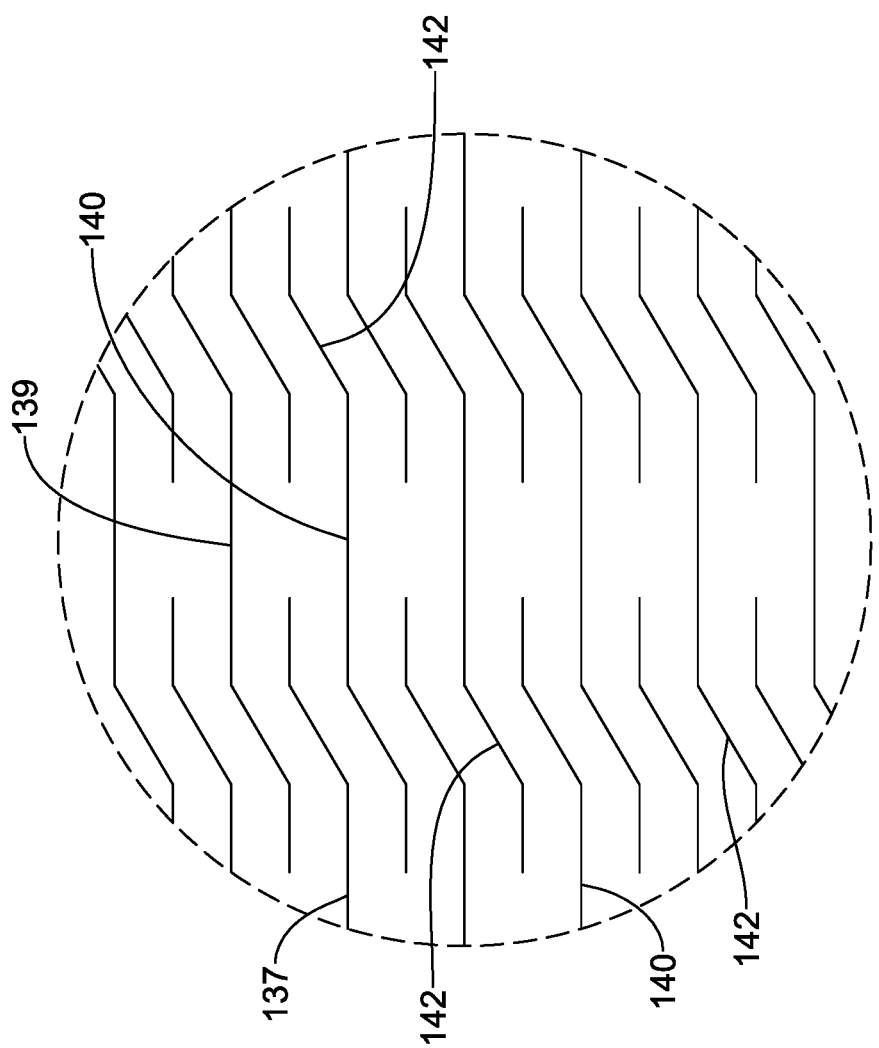
FIG. 3B shows an enlarged view of a region of the flat pattern of slits in FIG. 3A.

The entirety of each slit 130 may be linear. In other examples, the distal slits 137, proximal slits 138 (not shown in FIG. 3B), and middle slits 139 may have at least one linear portion 140 and at least one angled portion 142, as illustrated in FIG. 3B. In the example shown in FIG. 3B, the middle slits 139 have a single linear portion 140 flanked on either end by an angled portion 142. The angled portions 142 may include one or more non-zero angle. As illustrated, the angled portions 142 have two non-zero angles. In other examples, the slits 130 may have at least one linear portion and one or more curved or arced portions. For example, the angled portions 142 illustrated in FIG. 3B may be formed by a continuous curve or two curves separated by a linear portion.

Figure 4:
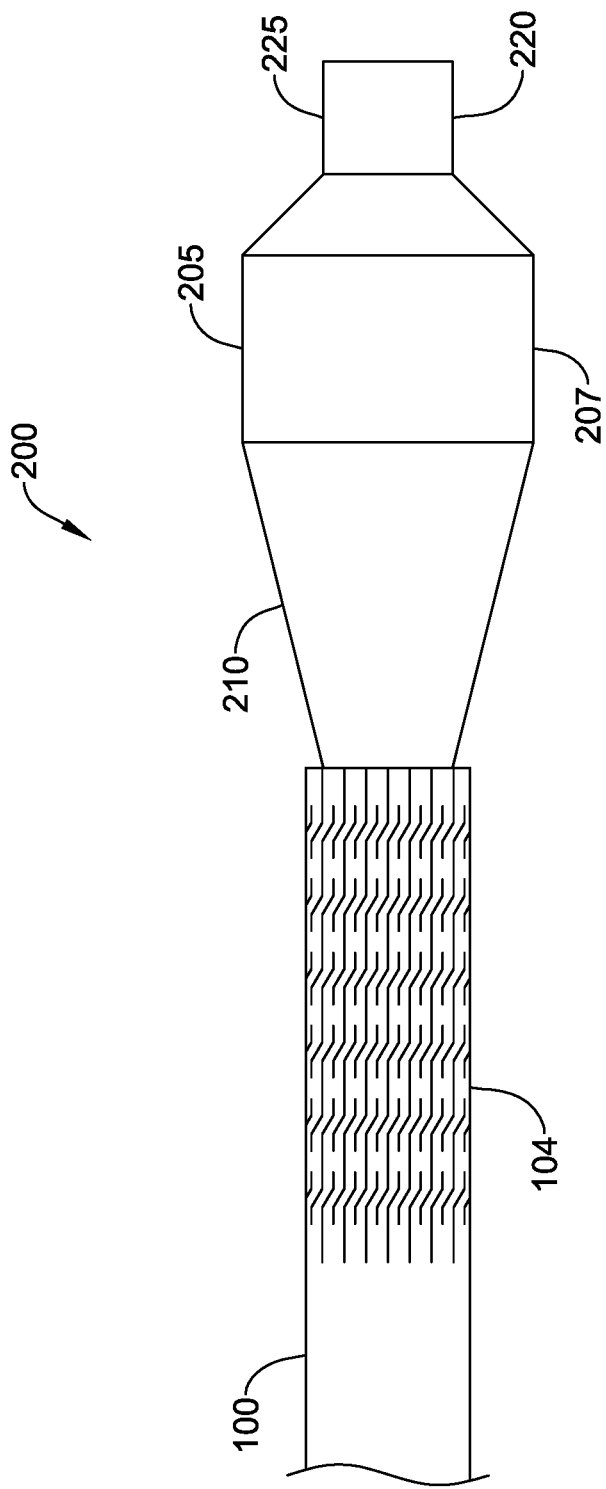
FIG. 4 illustrates an exemplary filter sheath and expansion balloon.

FIG. 4 illustrates an example embolic filtering device 200, including the filter sheath 100 slidingly disposed over a dilation shaft 220 with attached balloon 205. The balloon 205 is shown in an expanded configuration positioned distal of the filter sheath 100, in order to show the conical proximal end 210 that is configured to expand the expandable filter region 104 of the filter sheath 100. The balloon 205 may be molded to have a conical proximal end 210 shaped to match the final desired dimensions of the expandable filter region 104. The balloon 205 may have a short (1-2 mm) cylindrical body segment 207 distal of the conical proximal end 210. The cylindrical body segment 207 may taper down and be fixed to the dilation shaft 220.

The dilation shaft 220 may include a dilator 225 that may be comprised of three segments: proximal, mid, and distal. The balloon 205 may be bonded to the mid dilator segment, and thus the mid segment may have a smaller outer diameter compared to the distal and proximal segments, to accommodate for the bulk of the folded balloon 205, but the inner diameter will be consistent with the proximal and distal segments. A length of tubing (not shown) may be inset into the side of the dilation shaft 220 and may extend onto the mid segment, into the balloon 205 inner diameter. The tubing may act as the inflation lumen for the balloon 205. The distal dilator segment may have the same outer diameter as the proximal segment, but will not have the inset tubing. The distal tip of the distal segment may be tapered.

FIG. 5 illustrates the example embolic filtering device 200 of FIG. 4 in the expanded, flared configuration with the conical proximal end 210 of the balloon 205 disposed within the expandable filter region 104 of the filter sheath 100. The expanded balloon 205 has expanded the expandable filter region 104 to the flared configuration, widening the distal slits 137 to separate the distal sections 112 of the filter sheath 100 and widening the middle slits 139 to form holes 150.

Conventional treatment of a below the knee (BTK) artery obstruction or lesion may be achieved using a contralateral femoral access site. The ability to access and cross the lesion may present a challenging task to a physician given the smaller diameter vessels involved, tortuous anatomy of the leg vasculature, and structure of the lesion. For example, when treating vascular obstructions in smaller vessels (e.g., below the knee), placement of a guide wire across or within the lesion can be challenging due to relatively dense calcific, atheromatous plaque since conventional guide wires have relatively weak column strength (e.g., the guide wire often does not support the requisite amount of force for crossing the plaque without buckling or prolapsing).

Figure 6:
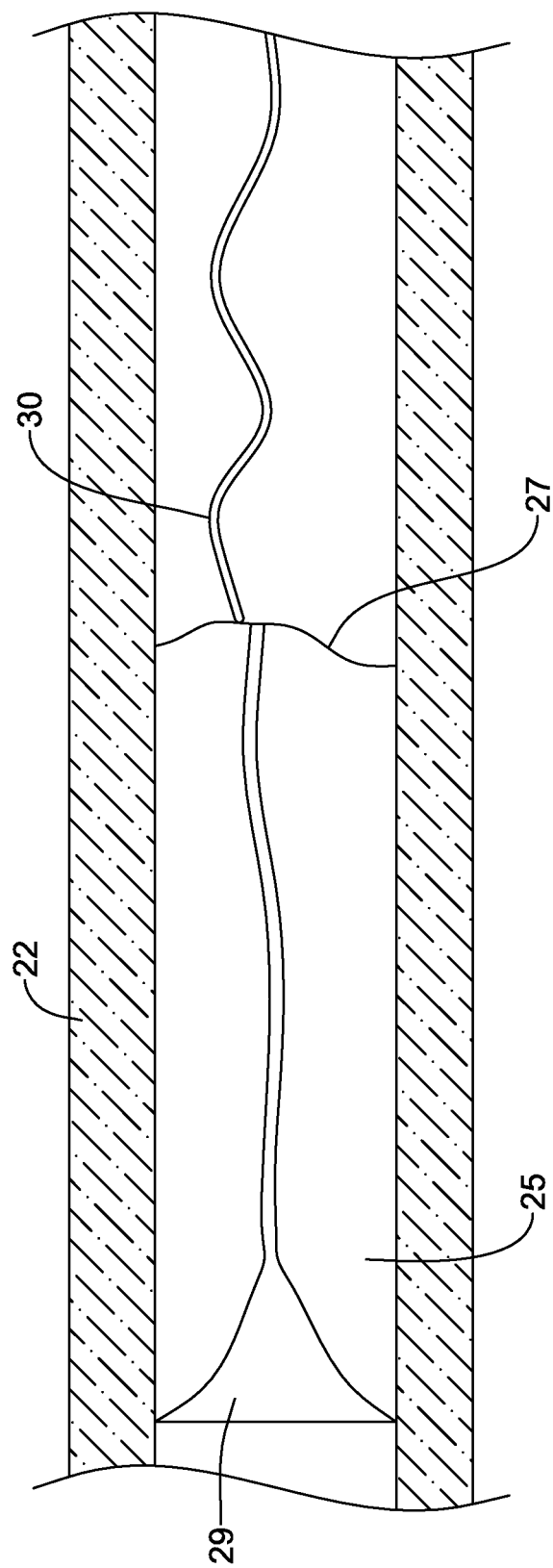
FIG. 6 is a cross sectional view of vessel lesion and guide wire approaching from upstream.

FIG. 6 illustrates a conventional upstream approach of a guide wire 30 from a femoral access site to a lesion 25 in a vessel 22 such as an artery below the knee. The issues of guide wire 30 pushability and buckling may further be complicated by the clinical observation that the upstream end 27 of the lesion 25, such as a plaque, or plaque cap in the case of a total occlusion, may be substantially flat or bulbous in addition to being more dense, calcific, or fibrous than the downstream end 29, which often has a v-shaped opening. This presents a challenge in directing the guide wire 30 across or within the lesion 25 from the upstream or antegrade approach.

Figure 7:
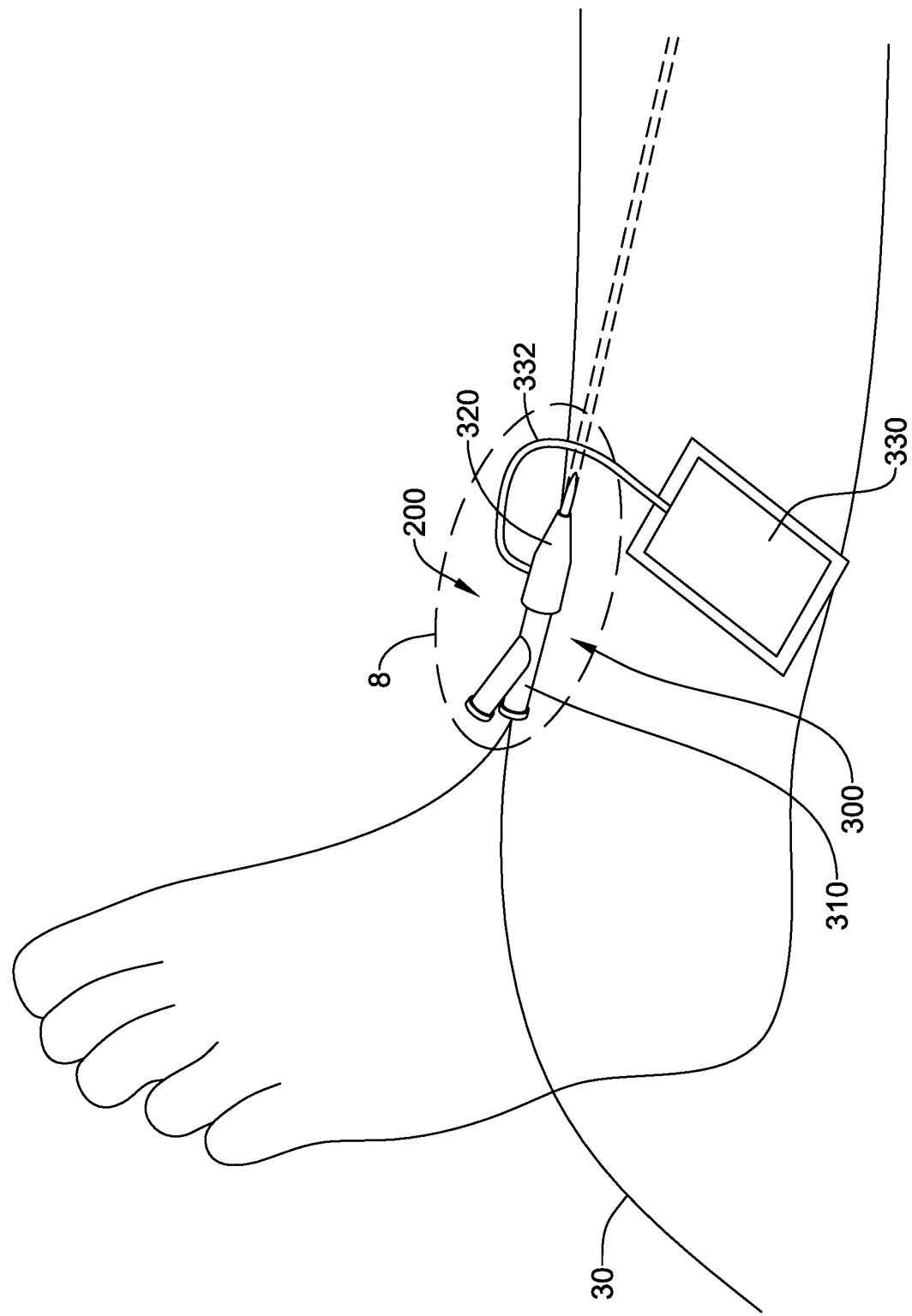
FIG. 7 illustrates portions of an exemplary embolic filtering device positioned outside the body during pedal access to a vessel.

The embolic filtering device 200 may provide access to the lesion via transpedal access using a retrograde approach, as shown in FIGS. 7-15. The embolic filtering device 200 may be inserted into a pedal artery downstream of the lesion using the Seldinger technique. The proximal portions of an example embolic filtering device 200 residing outside the body are illustrated in FIG. 7. A two part hub 300 is shown disposed over the guide wire 30. The hub 300 may include a proximal hub portion 310 and a distal hub portion 320. A collection bag 330 may be connected by a tube 332 to the distal hub portion 320. As seen in the close-up shown in FIG. 8, the distal hub portion 320 may be attached to a catheter 340 extending into the body. The filter sheath 100 may be disposed within the catheter 340. Alternatively, the distal hub portion 320 may be attached directly to the proximal end of the filter sheath 100. The distal hub portion 320 may include a port 324 through which the tube 332 extends and connects to the collection bag 330, shown in FIG. 7. The distal hub portion 320 may also include a slot 322 configured to receive a tab 312 on the proximal hub portion 310. The proximal hub portion 310 is connected to the dilation shaft 220 and is configured to rotate and slide within the distal hub portion 320, providing a twist-lock assembly for moving the dilation shaft 220 within the filter sheath 100 and expanding the expandable filter region 104. The proximal hub portion 310 may include a guide wire lumen 314 and an inflation lumen 316.

Figure 8:
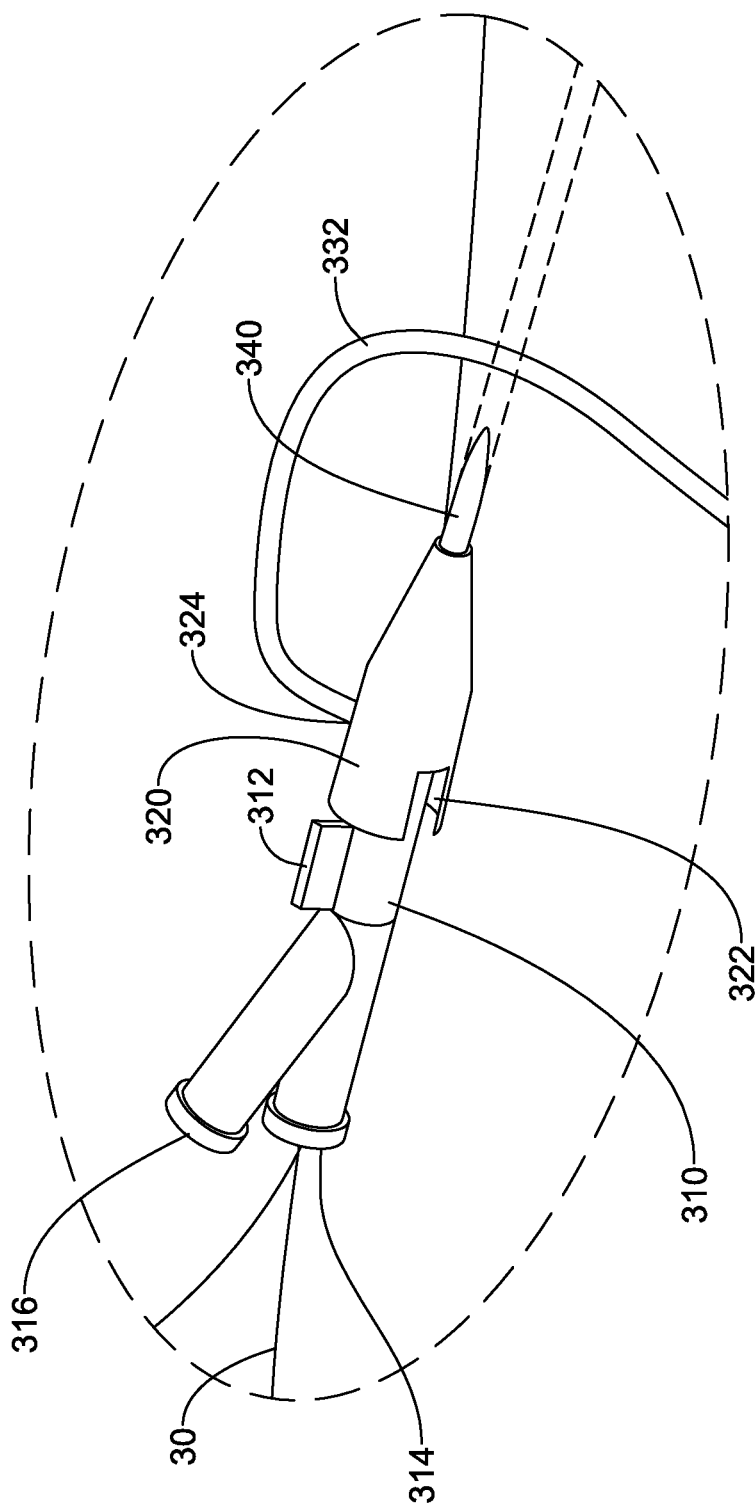
FIG. 8 is an enlarged view of the hub assembly of the embolic filtering device of FIG. 7 in a first position.
Figure 9:
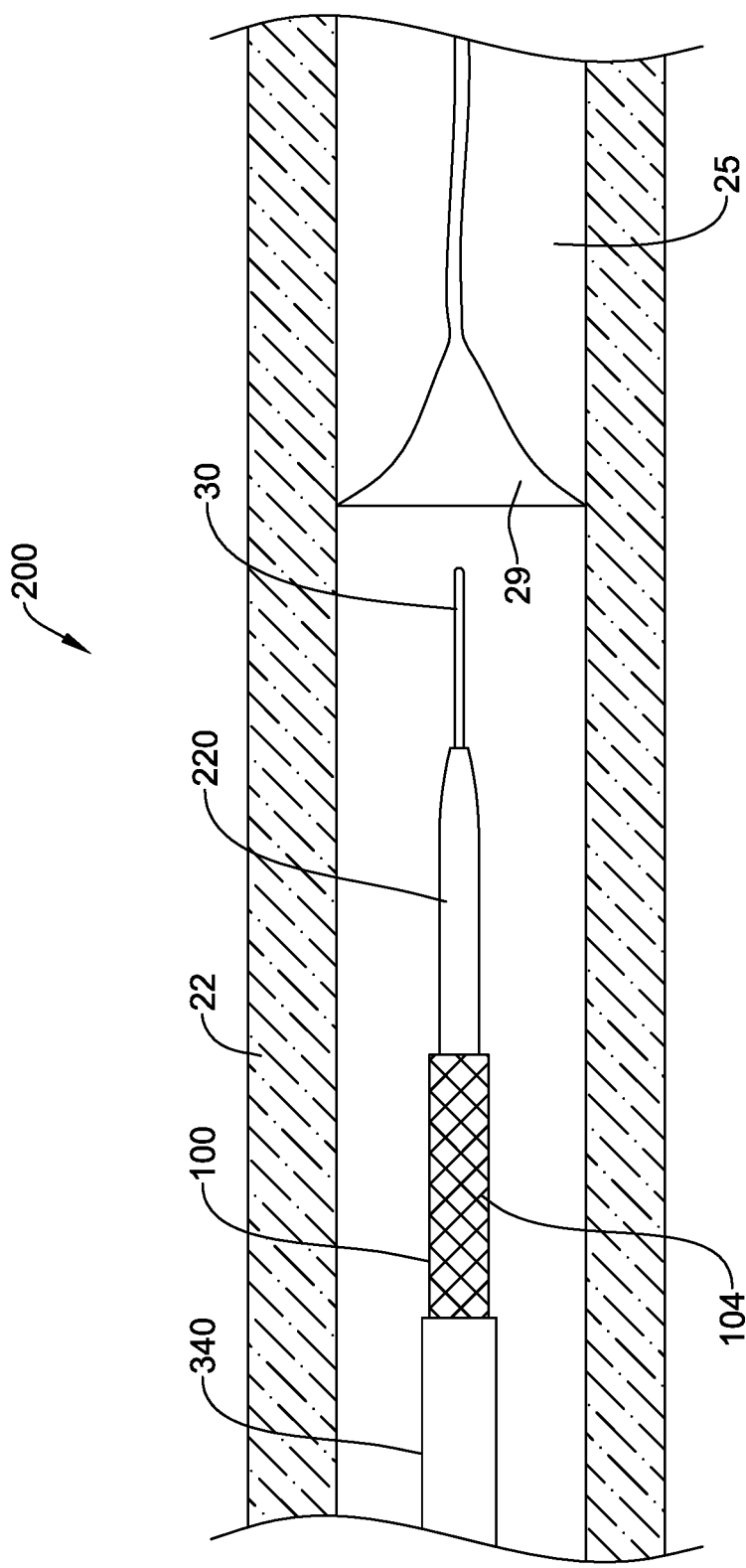
FIG. 9 is a cross sectional view of the embolic filtering device of FIG. 7 positioned in a vessel adjacent a lesion.

With the hub 300 in the configuration shown in FIG. 8, the embolic filtering device 200 extends through the catheter 340 and through the vessel 22 distal of the lesion 25, as shown in FIG. 9. The guide wire 30 extends through the dilation shaft 220 to a position adjacent the downstream end 29 of the lesion 25. The dilation shaft 220 extends through the expandable filter region 104 of the filter sheath 100, with the balloon disposed proximal of the expandable filter region 104. The filter sheath 100 extends through the catheter 340.

Figure 10:
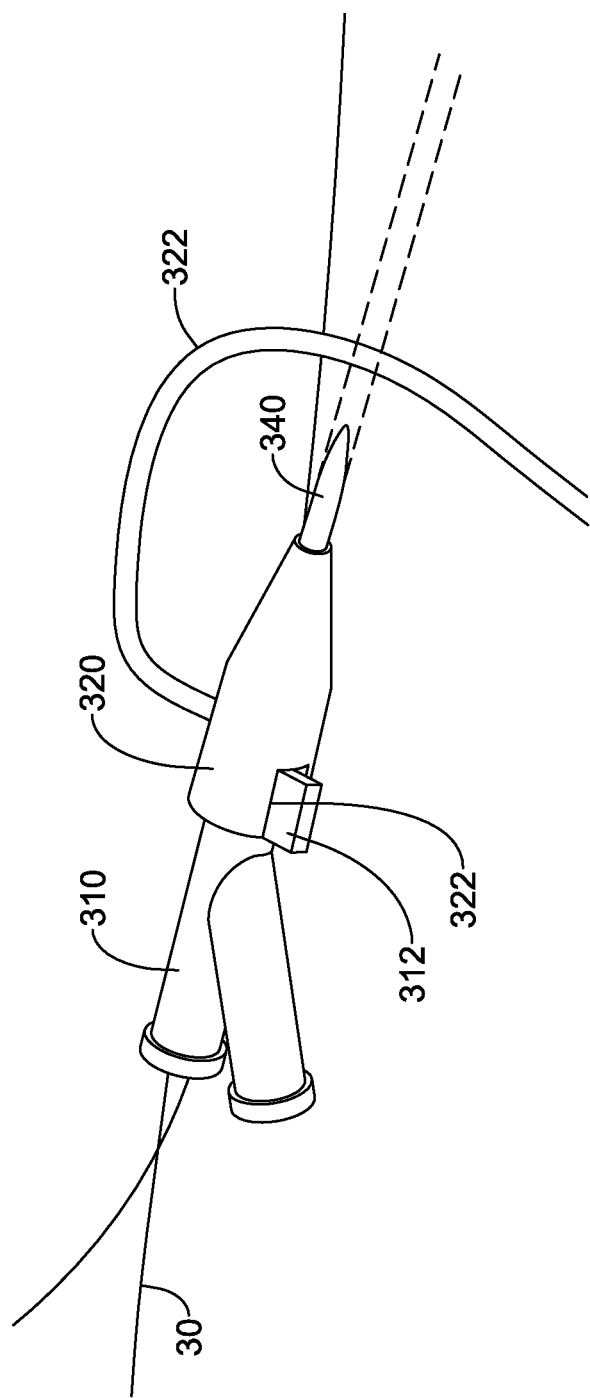
FIG. 10 illustrates the hub assembly of FIG. 8 moved to a second position.
Figure 11:
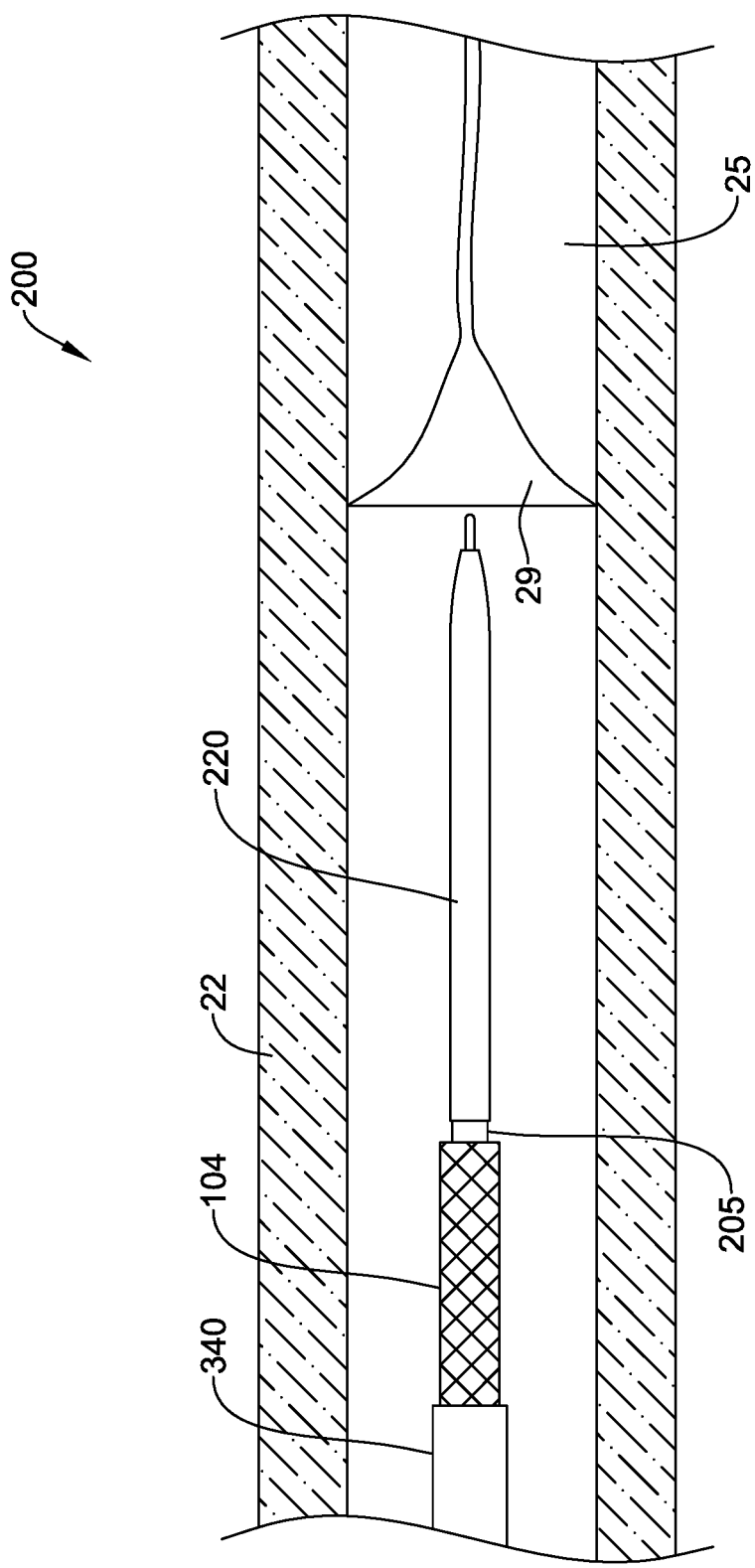
FIG. 11 is a cross sectional view of the embolic filter device of FIG. 9 with the dilator shaft advanced.
Figure 12:
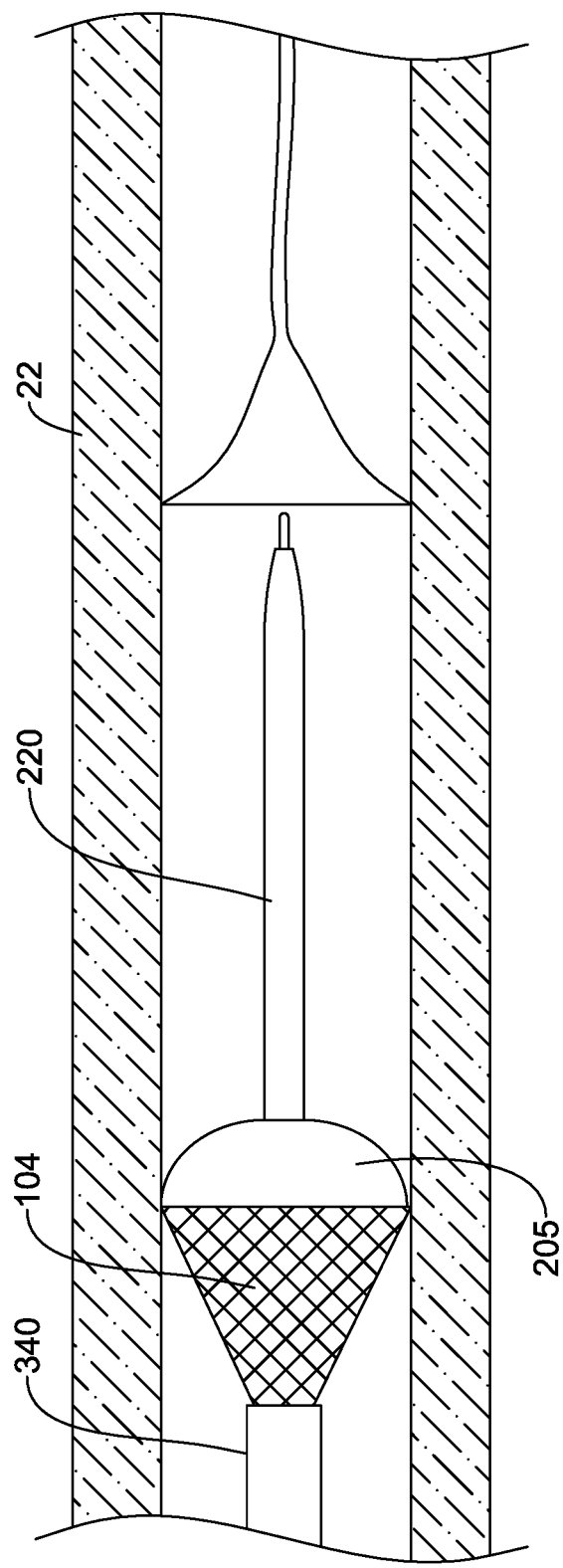
FIG. 12 is a cross sectional view of the embolic filter device of FIG. 11 with the balloon expanded.
Figure 13:
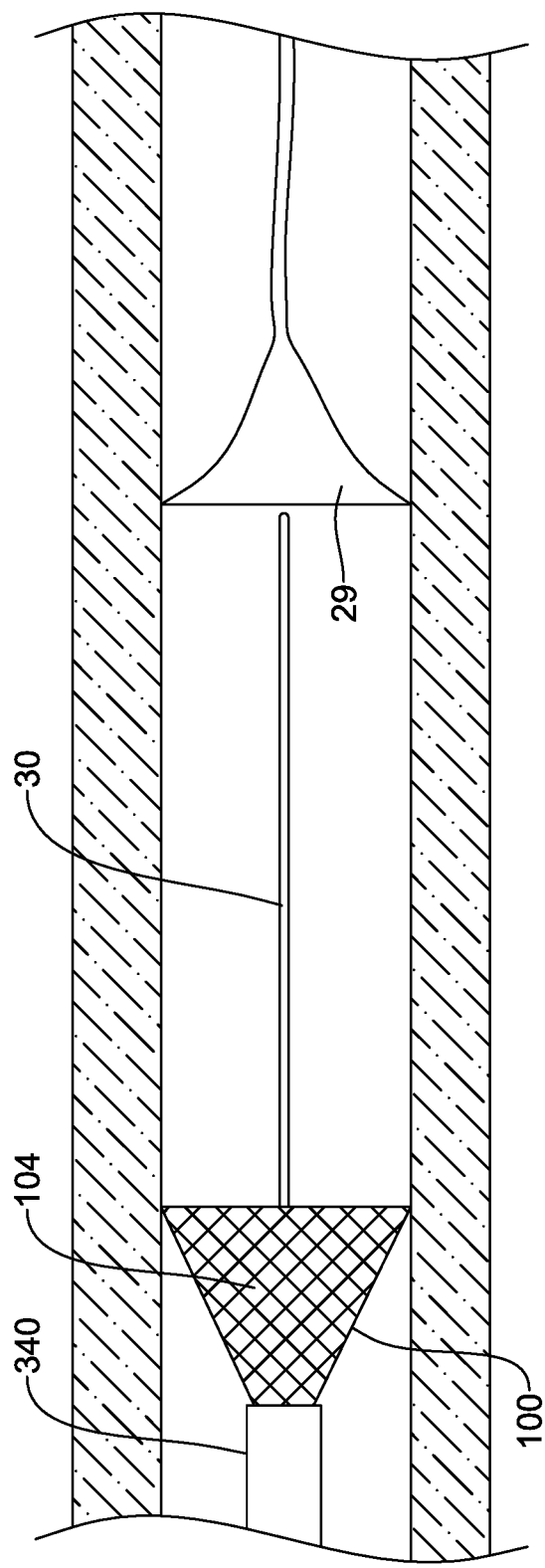
FIG. 13 is a cross sectional view of the embolic filter device of FIG. 12 with the dilation shaft removed.

With the embolic filtering device 200 in place downstream of the lesion 25, the proximal hub portion 310 may then be rotated and slid distally until the tab 312 slides into the slot 322 of the distal hub portion 320, as shown in FIG. 10. In this position, the proximal hub portion 310 is locked into the distal hub portion 320, preventing further distal movement of the dilation shaft 220. Sliding the proximal hub portion 310 distally into the distal hub portion 320 moves the dilation shaft 220 a predetermined distance out of the expandable filter region 104, positioning the balloon 205 within the expandable filter region 104, as shown in FIG. 11. Inflation of the balloon 205 causes expansion of the expandable filter region 104 until the edges of the expandable filter region 104 contact the vessel 22 walls, as shown in FIG. 12. The balloon 205 may then be deflated and the dilation shaft 220 withdrawn proximally, leaving the filter sheath 100 with its expandable filter region 104 in the expanded configuration, as shown in FIG. 13. The open lumen of the filter sheath 100 acts as an introducer sheath for insertion of atherectomy or other endovascular CLI treatment devices, while the expandable filter region 104 prevents plaque particles from traveling downstream and allows for the particles to be collected in the collection bag 330 located external of the body, as shown in FIG. 7.

Figure 14:
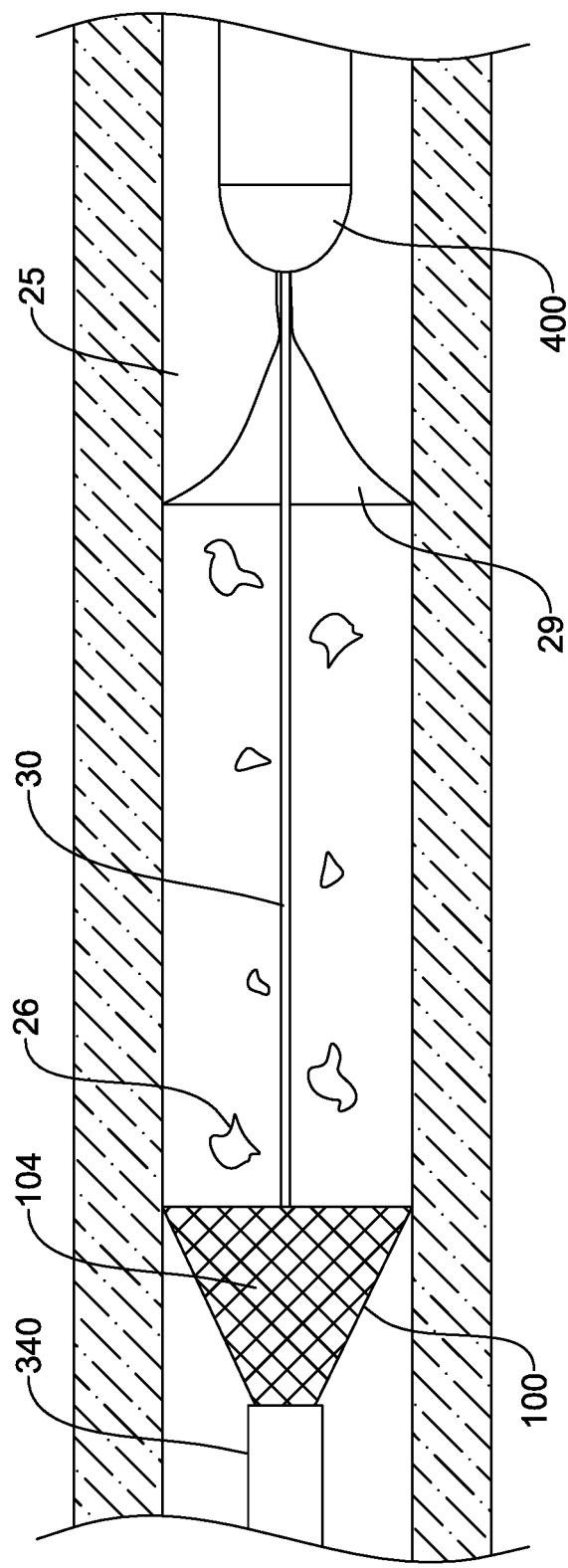
FIG. 14 is a cross sectional view of the embolic filter device of FIG. 13 showing an ablation device and released lesion particles.
Figure 15:
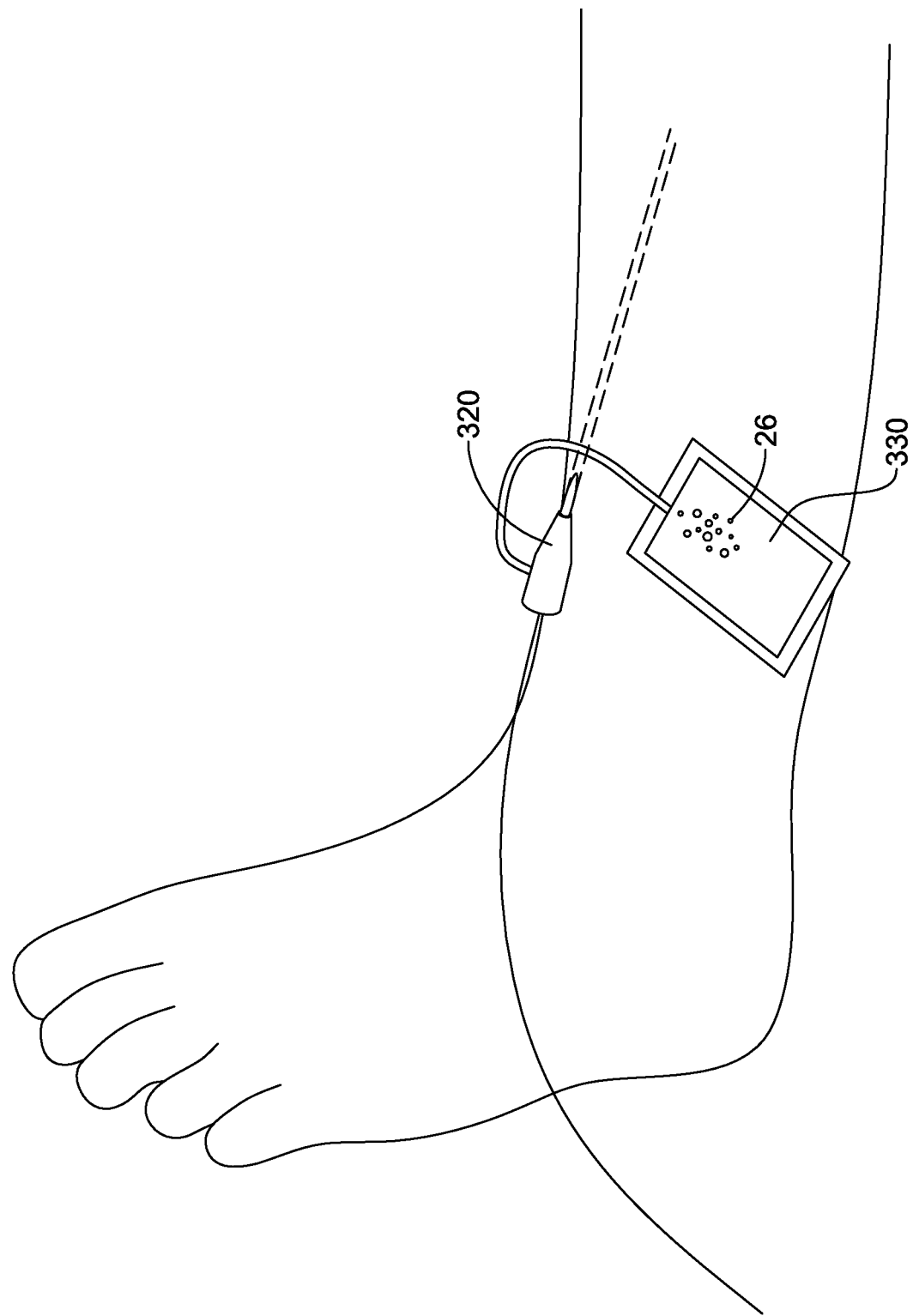
FIG. 15 illustrates the embolic filtering device of claim 7 with lesion particles in the collection bag.

In one example, once the expandable filter region 104 has been expanded, the guide wire 30 may then be advanced through the lesion 25. This pedal approach may provide the advantage of allowing for the entry of the guide wire 30 into the downstream end 29 of the lesion, which may have a v-shaped opening, providing easier access than the upstream end 27, which is often flat or bulbous, as shown in FIG. 6. The guide wire 30 may be extended to a femoral access site, and used to guide an ablation device 400 from the femoral access site to the lesion 25. As shown in FIG. 14, the ablation device 400 may be moved through the lesion 25, with particles 26 of the lesion being trapped by the expandable filter region 104 while blood flows through the expandable filter region 104 and past the catheter 340. The particles 26 may be drained through the filter sheath 100 to the collection bag 330 connected to the distal hub portion 320, as shown in FIG. 15. The particles 26 may be passively drained into the collection bag 330 or they may be actively aspirated by a syringe or applicable suction device.

Due to the open shaft structure of the filter sheath 100, if a large particle blocks the shaft, a tool (not shown) may be inserted through the filter sheath 100 to push the large particle back out through the expandable filter region 104 and into the ablation/grinding device 400 to be broken into smaller particles 26 that may pass through the filter sheath 100 and into the collection bag 330.

The combination of pedal access and femoral access may allow the ablation device 400 or other treatment device to be pushed or pulled from the femoral access site to cross the lesion as opposed to being pushed towards the lesion from the pedal access site. Pulling the treatment device across the lesion from the upstream end 27 to the downstream end 29 may provide better leverage and crossing force as opposed to pushing the treatment device, since the application of a tensile load will not be likely to buckle or otherwise compress the treatment device.

In other examples, the ablation device 400 or other lesion treating devices may be advanced through the filter sheath 100 from the pedal access site to the downstream end 29 of the lesion 25, with the expanded expandable filter region 104 preventing particles from traveling to the smaller vessels of the foot where they might create a blockage. The filter sheath 100 provides access for various treatment devices while also providing filtration at the distal end, without the need for a separate introducer sheath and filtration device. It is noted that while the above discussion describes the benefits of utilizing the filter sheath 100 in a below the knee atherectomy procedure, it is contemplated that the filter sheath 100 may be utilized in other portions of the body.

Figure 16:
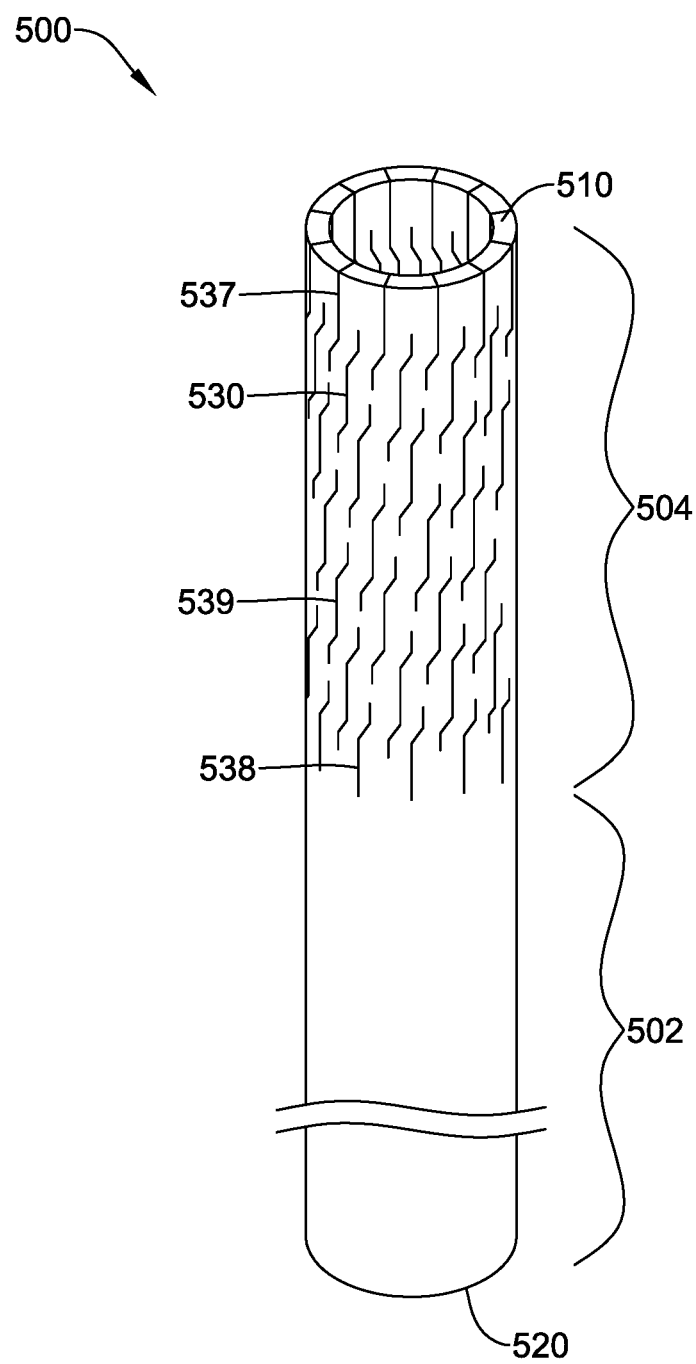
FIG. 16 illustrates another example filter sheath for use during an atherectomy procedure.

The sheaths illustrated in FIGS. 16-21 are similar to the sheath 100 illustrated in FIGS. 1-3B, but with different patterns and shapes of slits. Specifically, FIG. 16 illustrates another example filter sheath 500 having a distal end 510, a proximal end 520, a solid walled region 502 and an expandable filter region 504. The solid walled region 502 extends from the proximal end 520 to the expandable filter region 504. The solid walled region 502 may be defined by a solid tubular shaft devoid of any slits, holes or openings extending through the wall.

The expandable filter region 504 may be located adjacent the distal end 510 of the filter sheath 500 and may be defined by a plurality of slits 530 extending completely through the wall of the filter sheath 500. The plurality of slits 530 may be present in a pattern and may include a set of circumferentially spaced apart distal slits 537, a set of circumferentially spaced apart proximal slits 538 and at least one set of circumferentially spaced apart middle slits 539.

Figure 17:
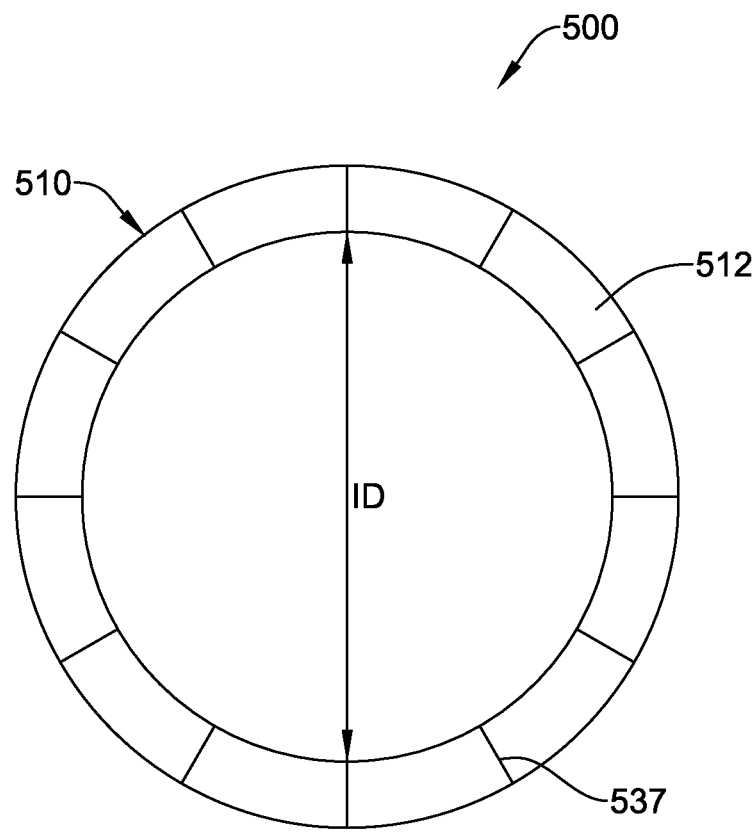
FIG. 17 is a top view of the filter sheath of FIG. 16.

FIG. 17 illustrates a top view of the distal end 510 of the filter sheath 500 having an inner diameter ID. As shown, the distal slits 537 extend to the very distal end 510 of the sheath, separating the distal end 510 into a number of separate distal sections 512. In the example shown in FIG. 17, the filter sheath 500 has twelve distal slits 537 that divide the distal end 510 into twelve distal sections 512.

Figure 18:
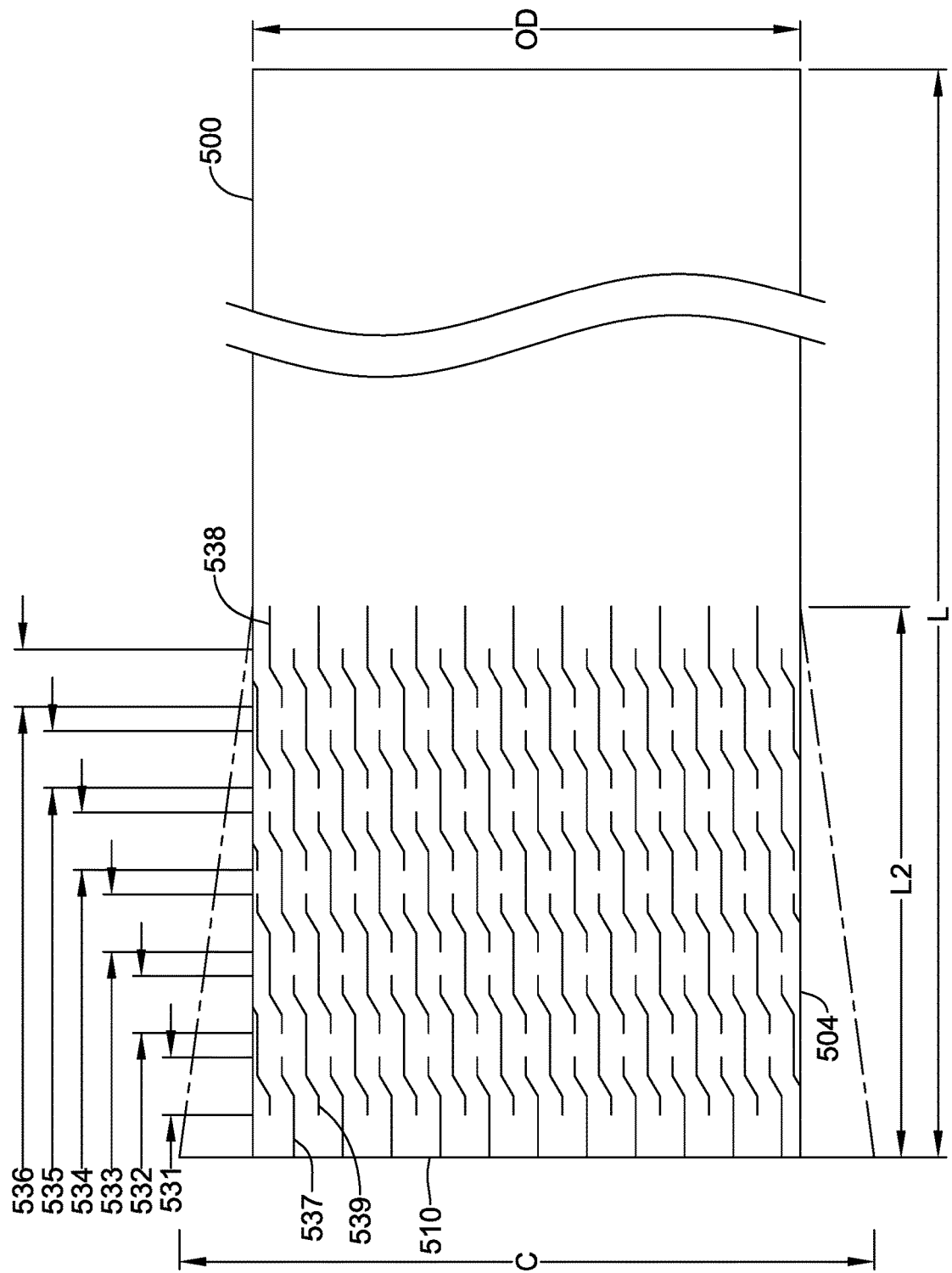
FIG. 18 illustrates a flat pattern of slits of the filter sheath of FIG. 16.

The plurality of slits 530 may form a plurality of overlap regions 531-536, as shown in FIG. 18. As illustrated, a portion of each of the distal slits 537 overlaps a portion of a first set of middle slits 539 in overlap region 531. Similarly, a portion of the first set of middle slits 539 overlaps a portion of the next set of middle slits in overlap region 532. In the example slit pattern illustrated in FIG. 18, the distal slits 537, five sets of middle slits 539, and proximal slits 538 overlap in six overlap regions 531, 532, 533, 534, 535, and 536. Each of the six overlap regions 531-536 may have a different longitudinal length, the same longitudinal length, or some overlap regions may have the same longitudinal length and other overlap regions may have different longitudinal lengths. In one example, the first overlap region 531 may have a longitudinal length of 0.497 mm, the second overlap region 532 may have a longitudinal length of 0.479 mm, the third overlap region 533 may have a longitudinal length of 0.462 mm, the fourth overlap region 534 may have a longitudinal length of 0.444 mm, the fifth overlap region 535 may have a longitudinal length of 0.427 mm, and the sixth overlap region 536 may have a longitudinal length of 0.409 mm. The filter sheath 500 may have a total length L of 130 mm, an outer diameter OD of 1.78 mm and an inner diameter ID of 1.41 mm in the contracted configuration shown in FIGS. 16 and 17. The filter sheath 500 may have a maximum circumference C at the distal end 510, when stretched, of 7.374 mm. The length L2 of the expandable filter region 504 may be 5.34 mm.

Figure 19:
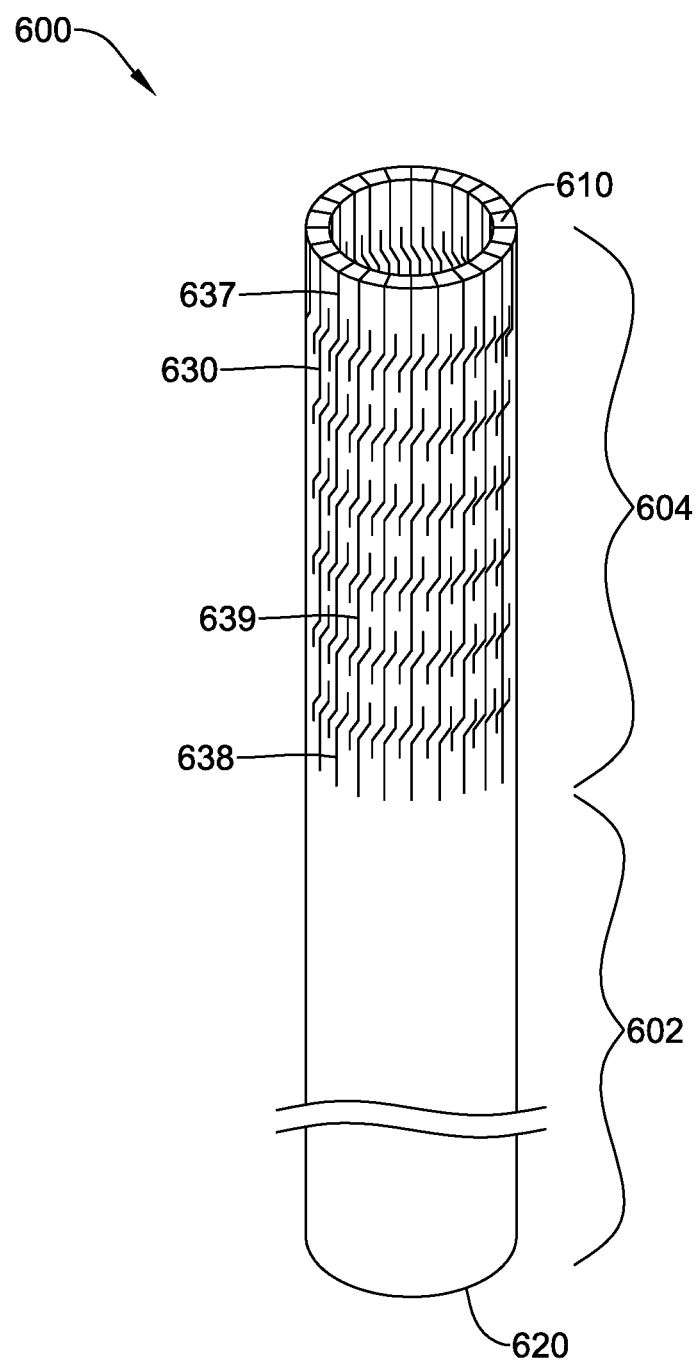
FIG. 19 illustrates a further example filter sheath for use during an atherectomy procedure.

FIG. 19 illustrates a further example filter sheath 600 having a distal end 610, a proximal end 620, a solid walled region 602 and an expandable filter region 604. The solid walled region 602 extends from the proximal end 620 to the expandable filter region 604. The solid walled region 602 may be defined by a solid tubular shaft devoid of any slits, holes or openings extending through the wall.

The expandable filter region 604 may be located adjacent the distal end 610 of the filter sheath 600 and may be defined by a plurality of slits 630 extending completely through the wall of the filter sheath 600. The plurality of slits 630 may be present in a pattern and may include a set of circumferentially spaced apart distal slits 637, a set of circumferentially spaced apart proximal slits 638 and at least one set of circumferentially spaced apart middle slits 639.

Figure 20:
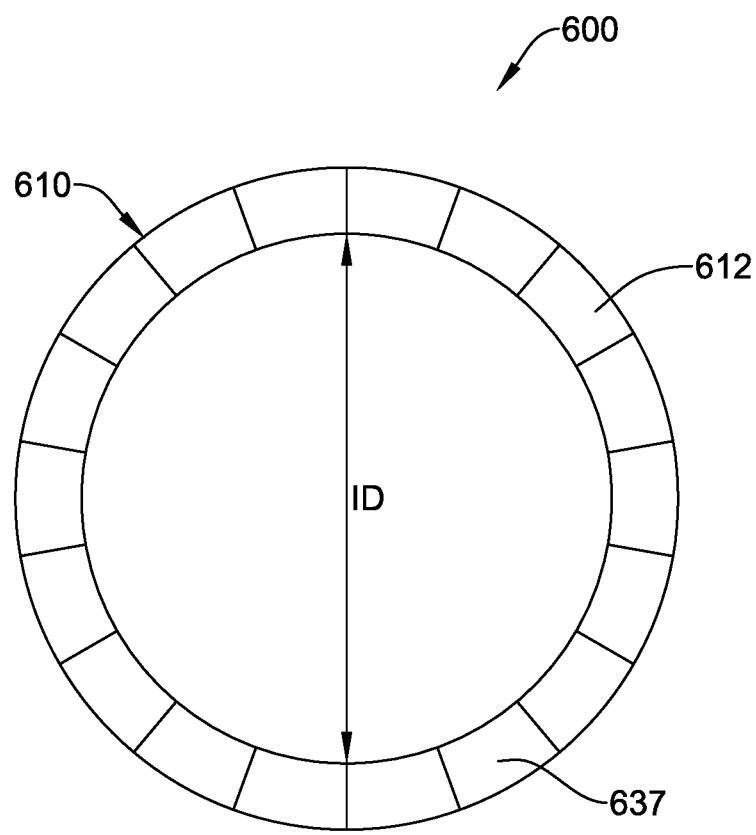
FIG. 20 is a top view of the filter sheath of FIG. 19.

FIG. 20 illustrates a top view of the distal end 610 of the filter sheath 600 having an inner diameter ID. As shown, the distal slits 637 extend to the very distal end 610 of the sheath, separating the distal end 610 into a number of separate distal sections 612. In the example shown in FIG. 20, the filter sheath 600 has eighteen distal slits 637 that divide the distal end 610 into eighteen distal sections 612.

Figure 21:
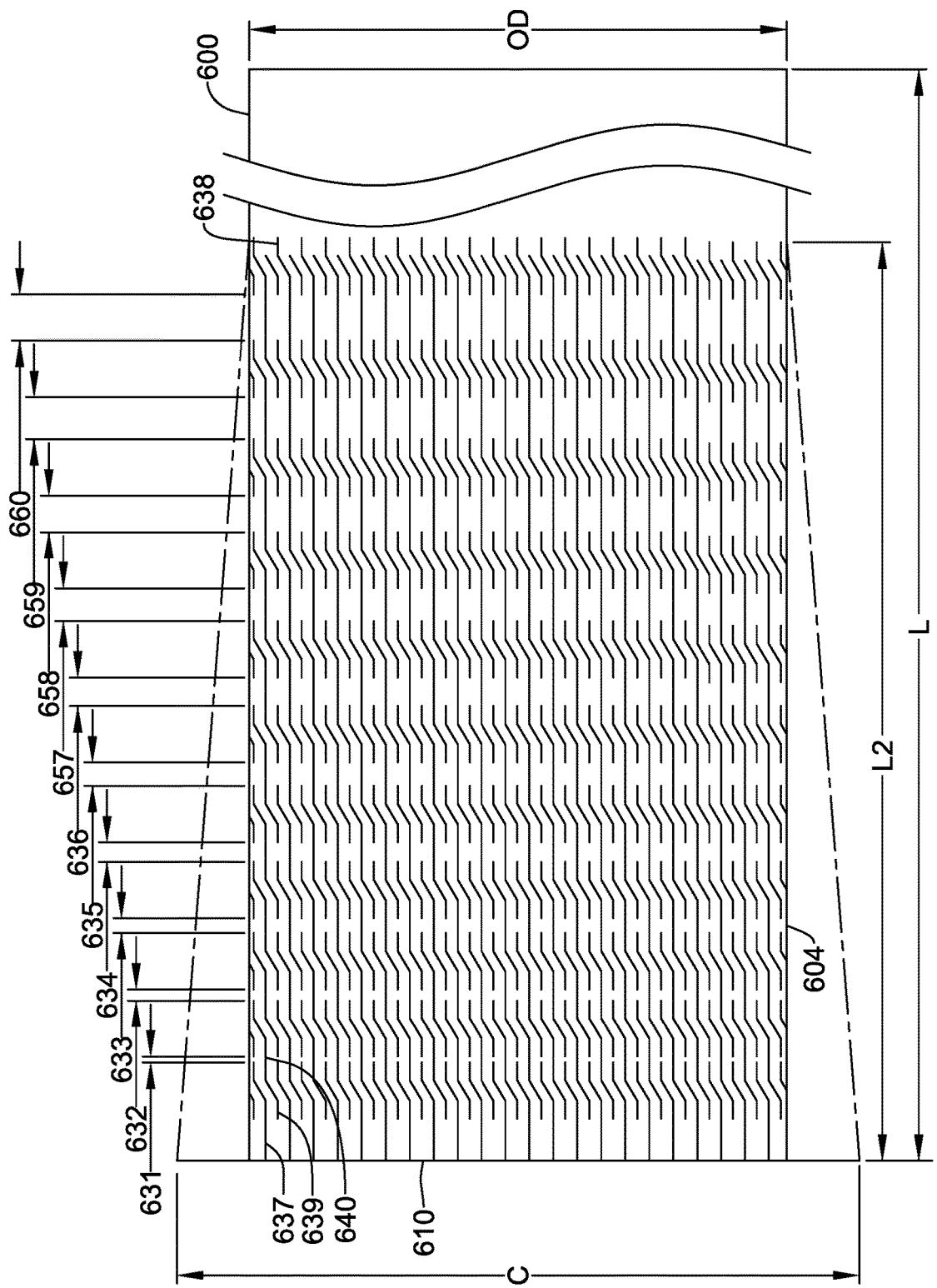
FIG. 21 illustrates a flat pattern of slits of the filter sheath of FIG. 19.

The plurality of slits 630 may form a plurality of overlapping regions. However, instead of illustrating the differing lengths of the overlapping regions, as in FIG. 18, FIG. 21 illustrates the plurality of spacing regions 631, 632, 633, 634, 635, 636, 657, 658, 659, 660, which are regions in which only the middle portion 640 of a circumferential set of middle slits 639 is found. In the example slit pattern illustrated in FIG. 21, the distal slits 637, ten sets of middle slits 639, and proximal slits 638 are arranged in a pattern. The proximal ends of the distal slits 637 are separated from the distal ends of the second set of middle slits 639 by spacing region 631. The proximal ends of the first set of middle slits 639 are separated from the distal ends of the third set of middle slits by spacing region 632. The proximal ends of the second set of middle slits 639 are separated from the distal ends of the fourth set of middle slits by spacing region 633. The proximal ends of the third set of middle slits 639 are separated from the distal ends of the fifth set of middle slits by spacing region 634. The proximal ends of the fourth set of middle slits 639 are separated from the distal ends of the sixth set of middle slits by spacing region 635. The proximal ends of the fifth set of middle slits 639 are separated from the distal ends of the seventh set of middle slits by spacing region 636. The proximal ends of the sixth set of middle slits 639 are separated from the distal ends of the eighth set of middle slits by spacing region 657. The proximal ends of the seventh set of middle slits 639 are separated from the distal ends of the ninth set of middle slits by spacing region 658. The proximal ends of the eighth set of middle slits 639 are separated from the distal ends of the tenth set of middle slits by spacing region 659. The proximal ends of the ninth set of middle slits 639 are separated from the distal ends of the proximal slits 638 by spacing region 660.

Each of the ten spacing regions 631, 632, 633, 634, 635, 636, 657, 658, 659, 660 may have a different longitudinal length, the same longitudinal length, or some overlap regions may have the same longitudinal length and other overlap regions may have different longitudinal lengths. In one example, the first spacing region 631 may have a longitudinal length of 0.095 mm, the second spacing region 632 may have a longitudinal length of 0.104 mm, the third spacing region 633 may have a longitudinal length of 0.112 mm, the fourth spacing region 634 may have a longitudinal length of 0.121 mm, the fifth spacing region 635 may have a longitudinal length of 0.130 mm, the sixth spacing region 636 may have a longitudinal length of 0.139 mm, the seventh spacing region 657 may have a longitudinal length of 0.147 mm. The eighth spacing region 658 may have a longitudinal length of 0.156 mm, the ninth spacing region 659 may have a longitudinal length of 0.165 mm, and the tenth spacing region 660 may have a longitudinal length of 0.174 mm. The spacing regions may thus decrease in length from the proximal end to the distal end of the expandable filter region 604, providing greater expansion at the distal end 610 of the filter sheath 600 as compared to the region of the proximal slits 638.

The filter sheath 600 may have a total length L of 130 mm, an outer diameter OD of 1.78 mm and an inner diameter ID of 1.41 mm in the contracted configuration shown in FIGS. 19 and 20. The filter sheath 600 may have a maximum circumference C at the distal end 610, when stretched, of 7.374 mm. The length L2 of the expandable filter region 604 may be 5.34 mm.

It will be understood that the dimensions described in association with the above figure are illustrative only, and that other dimensions of slits and filter sheaths are contemplated. The materials that can be used for the various components of the embolic filtering device 200 for capturing lesion particles (and/or other systems or components disclosed herein) and the various elements thereof disclosed herein may include those commonly associated with medical devices. For simplicity purposes, the following discussion makes reference to the embolic filtering device 200 (and variations, systems or components disclosed herein). However, this is not intended to limit the devices and methods described herein, as the discussion may be applied to other elements, members, components, or devices disclosed herein.

In some embodiments, the embolic filtering device 200 (and variations, systems or components thereof disclosed herein) may be made from a metal, metal alloy, ceramics, zirconia, polymer (some examples of which are disclosed below), a metal-polymer composite, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; cobalt chromium alloys, titanium and its alloys, alumina, metals with diamond-like coatings (DLC) or titanium nitride coatings, other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the embolic filtering device 200 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the embolic filtering device 200 (and variations, systems or components thereof disclosed herein).

Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the embolic filtering device 200 (and variations, systems or components thereof disclosed herein) to achieve the same result.

In some embodiments, the embolic filtering device 200 (and variations, systems or components thereof disclosed herein) and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the embolic filtering device 200 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An embolic filtering assembly comprising:
  a filtering sheath comprising an elongated tubular member defined by a circumferential wall and having a distal end and a proximal end, the filtering sheath having a lumen extending longitudinally between the distal and proximal ends, the distal end having a plurality of slits extending through the circumferential wall, the plurality of slits defining an expandable filter region, wherein the plurality of slits are arranged in a pattern that allows the expandable filter region to move between a first, contracted configuration, and a second, expanded configuration;
  a dilation shaft having a dilator on a distal end thereof, and a balloon attached to the dilator, the dilation shaft removably disposed within the lumen of the filtering sheath, wherein the balloon is configured to inflate and expand the expandable filter region; and
  a locking hub attached to the proximal end of the filtering sheath and the dilation shaft, wherein the locking hub includes a distal portion and a proximal portion, wherein the proximal portion is configured to rotate within and slide into and out of the distal portion, wherein the distal portion of the locking hub is fixed to the filtering sheath and the proximal portion of the locking hub is fixed to the dilation shaft, and wherein the distal portion of the locking hub includes a slot and the proximal portion of the locking hub includes a tab configured to enter the slot, thereby advancing the dilation shaft and positioning the balloon within the expandable filter region of the filtering sheath.

2. The embolic filtering assembly of claim 1, wherein the elongated tubular member, including the expandable filter region, is formed of a single monolithic piece.

* * * * *